(12) United States Patent
Zhang et al.

(10) Patent No.: US 9,181,207 B2
(45) Date of Patent: Nov. 10, 2015

(54) METHOD OF REDUCING OR MAINTAINING THE VALUE OF AN ALKYLENE OXIDE PRODUCTION PARAMETER IN A PROCESS OF MAKING AN ALKYLENE OXIDE USING A HIGH EFFICIENCY CATALYST

(71) Applicant: Dow Technology Investments LLC, Midland, MI (US)

(72) Inventors: Liping Zhang, Lake Jackson, TX (US); Sasanka Raha, Magarpatta (IN); Biju M. Devassy, Karukutty (IN); Balu S. Uphade, Pune (IN); Arun G. Basrur, Pune (IN); Ailene Gardner Phillips, Charleston, WV (US); Ravindra Tupe, Helsinki (FI)

(73) Assignee: Dow Technology Investments LLC, Midland, MI (US)

(*) Notice: Subject to any disclaimer, the term of this patent is extended or adjusted under 35 U.S.C. 154(b) by 0 days.

(21) Appl. No.: 14/363,388

(22) PCT Filed: Dec. 6, 2012

(86) PCT No.: PCT/US2012/068089
§ 371 (c)(1),
(2) Date: Jun. 6, 2014

(87) PCT Pub. No.: WO2013/086081
PCT Pub. Date: Jun. 13, 2013

(65) Prior Publication Data
US 2014/0316150 A1     Oct. 23, 2014

(30) Foreign Application Priority Data

Dec. 9, 2011 (IN) .............. 4303/CHE/2011

(51) Int. Cl.
*C07D 301/10* (2006.01)

(52) U.S. Cl.
CPC .................... *C07D 301/10* (2013.01)

(58) Field of Classification Search
CPC ..................................... C07D 301/10
USPC .......................................... 549/534
See application file for complete search history.

(56) References Cited

U.S. PATENT DOCUMENTS

| | | |
|---|---|---|
| 5,187,140 A | 2/1993 | Thorsteinson et al. |
| 6,717,001 B2 | 4/2004 | Evans et al. |

(Continued)

FOREIGN PATENT DOCUMENTS

| | | |
|---|---|---|
| CA | 1286689 | 7/1991 |
| CN | 1437590 A | 8/2003 |

(Continued)

OTHER PUBLICATIONS

English Translation of CN1437590A from Lexis Nexis Total Patent, Aug. 2003.

(Continued)

*Primary Examiner* — T. Victor Oh
(74) *Attorney, Agent, or Firm* — Hansen IP Law PLLC

(57) ABSTRACT

Methods of reducing or maintaining the value of an alkylene oxide production parameter (such as alkylene oxide production rate) in a process of making an alkylene oxide by reacting an alkylene and oxygen over a high efficiency catalyst are shown and described. One method comprises reducing the concentration of oxygen in the reactor feed gas to reduce or maintain the value of the alkylene oxide production parameter.

15 Claims, 14 Drawing Sheets

(56) References Cited

U.S. PATENT DOCUMENTS

| | | |
|---|---|---|
| 7,235,677 B2 | 6/2007 | Chipman et al. |
| 7,348,444 B2 | 3/2008 | Evans et al. |
| 7,507,845 B1 | 3/2009 | Gueckel |
| 7,553,980 B2 | 6/2009 | Rizkalla et al. |
| 7,615,655 B2 | 11/2009 | Zhang et al. |
| 7,657,331 B2 | 2/2010 | Chipman et al. |
| 2004/0014999 A1 | 1/2004 | Chipman et al. |
| 2010/0267972 A1 | 10/2010 | Zhang et al. |
| 2010/0267974 A1 | 10/2010 | Zhang et al. |
| 2010/0267975 A1 | 10/2010 | Habenschuss et al. |
| 2013/0245296 A1 | 9/2013 | Zhang et al. |

FOREIGN PATENT DOCUMENTS

| | | |
|---|---|---|
| EP | 0357292 A1 | 3/1990 |
| EP | 0352850 B1 | 1/1994 |
| EP | 1458699 B1 | 11/2005 |
| EP | 1292587 B1 | 10/2006 |
| WO | 0196324 A2 | 12/2001 |
| WO | 2008141030 A1 | 11/2008 |
| WO | 2009042300 A1 | 4/2009 |
| WO | 2009137431 A2 | 11/2009 |
| WO | 2010123842 A1 | 10/2010 |
| WO | 2010123844 A1 | 10/2010 |
| WO | 2010123856 A1 | 10/2010 |
| WO | 2012078948 A1 | 6/2012 |
| WO | 2012149098 A1 | 11/2012 |
| WO | 2013086081 A1 | 6/2013 |

OTHER PUBLICATIONS

Barteau, et al., Ethylene Epoxidation Over Silver and Copper—Silver Bimetallic Catalysts: II Cs and Cl Promotion, Journal of Catalysis 236 (2005) pp. 379-386.
International Search Report and Written Opinion dated, Apr. 2, 2012.
International Preliminary Report on Patentability (IPRP) dated, Dec. 3, 2012.
Amendment and Response to Written Opinion, as-filed dated, Sep. 25, 2012.
Othmer, Kirk, "Ethylene Oxide", Encyclopedia of Chemical Technology, vol. 10, pp. 632-673 (Feb. 14, 2005).
International Preliminary Report on Patentability (IPRP) dated, Mar. 3, 2014.
International Search Report and Written Opinion dated, Feb. 14, 2013.
Response to Written Opinion as-filed dated, Jan. 14, 2014.

METHOD OF REDUCING OR MAINTAINING THE VALUE OF AN ALKYLENE OXIDE PRODUCTION PARAMETER IN A PROCESS OF MAKING AN ALKYLENE OXIDE USING A HIGH EFFICIENCY CATALYST

TECHNICAL FIELD

This disclosure relates generally to processes for making alkylene oxides, and more specifically, to methods of reducing or maintaining the value of an alkylene oxide production parameter (i.e., a variable that relates to the extent to which alkylene oxides are produced) in alkylene oxide production processes using high efficiency catalysts.

BACKGROUND

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

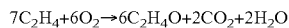

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than 0.1%/ppm) over a wide range of promoter concentrations, and this invariance is substantially unaltered as reaction temperature is changed (i.e., the change in efficiency with respect to a change in reaction temperature is less than 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least 0.2%/ppm when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age as well as other conditions such as feed gas composition. Moreover, the efficiency curves and the optimum gas phase promoter concentration tend to be strong functions of reaction temperature and are thus significantly affected if reaction temperature is varied, for example, to compensate for decreases in catalyst activity, (i.e., the change in efficiency with respect to a change in reaction temperature can be at least 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

Many commercial alkylene oxide processes are operated to achieve a targeted value of an alkylene oxide production parameter, such as the concentration of the alkylene oxide in the reaction product, alkylene oxide production rate, alkylene oxide production rate/catalyst volume (also known as the alkylene oxide "work rate"), alkylene oxide yield, alkylene conversion, and oxygen conversion. In order to maximize conversion of the alkylene, many known processes maintain the maximum reactor feed gas oxygen concentration that is allowable based on feed gas flammability considerations. Neither the alkylene nor oxygen are stoichiometrically limiting (i.e., neither of them are completely converted), and some amount of each is contained in the reaction product. When a reduction in the alkylene oxide production parameter is desired, reaction temperature is frequently reduced. The reduction in reaction temperature reduces the overall rate of consumption of alkylene and oxygen. However, it can also cause a significant shift in the efficiency of the process, resulting in the excessive generation of the unwanted byproducts carbon dioxide and water. Moreover, in certain cases, temperature cannot be used to control a desired alkylene oxide production parameter value. Alkylene oxide formation reactions are typically exothermic and require a coolant system to maintain a desired reaction temperature. The minimum achievable reaction temperature may be limited by the design and operability of the coolant system and may be higher than the temperature needed for the target production, resulting in overproduction of the alkylene oxide beyond that which is economically desirable or resulting in limitations in downstream recovery sections, such as a distillation section. While it may be possible to reduce gas phase promoter concentration to avoid such overproduction, underchloriding the catalyst can irreversibly impair catalyst efficiency. In addition, gas phase promoter concentrations are sometimes difficult to control to a degree necessary to maintain a desired alkylene oxide production parameter value due to their relatively low flow rates and the lack of sensitivity of available flow control systems. The problem tends to be more acute in the period following start-up when the activity of high efficiency catalysts tends to be high and/or the alkylene production target is low.

SUMMARY

In accordance with a first aspect of the present disclosure, a method for reducing the value of an alkylene oxide production parameter in a process for making the alkylene oxide by reacting a feed gas comprising an alkylene, oxygen, and at least one organic chloride over a high-efficiency silver catalyst is provided. The method comprises operating the process at a first reaction temperature, a first overall chloriding effectiveness, and a first concentration of oxygen in the feed gas to yield a first value of the alkylene oxide production parameter. The method further comprises selecting a target value of the alkylene oxide production parameter which is less than the first value of the alkylene oxide production parameter. At least one process parameter is adjusted such that the alkylene oxide production parameter decreases, wherein the step of adjusting at least one alkylene oxide production parameter comprises first decreasing the concentration of oxygen in the feed gas.

In accordance with a further aspect of the present disclosure, a method of maintaining a desired value of an alkylene oxide production parameter in a process for making the alkylene oxide by reacting a feed gas comprising an alkylene, oxygen, and at least one organic chloride over a high-efficiency silver catalyst is described. The method comprises the steps of selecting a target value of alkylene concentration in the feed gas and a target value of oxygen concentration in the feed gas, wherein the target value of the alkylene concentration in the feed gas, the target value of the oxygen concentration in the feed gas, and the desired value of the alkylene oxide production parameter correspond to a first reaction temperature. The method further comprises maintaining at least one selected from the group consisting of the alkylene concentration in the feed gas and the oxygen concentration in the feed gas below its corresponding target value to maintain the desired value of the alkylene oxide production parameter at a second reaction temperature. In certain examples, the second reaction temperature is a minimum reaction temperature as dictated by process constraints such as reactor cooling circuit capability limitations.

In accordance with an additional aspect of the present disclosure, a method of maintaining a desired value of an alkylene oxide production parameter in a process for making the alkylene oxide by reacting a feed gas comprising an alkylene, oxygen, and at least one organic chloride over a high-efficiency silver catalyst is described. The method comprises the steps of selecting a target value of alkylene concentration in the feed gas, a target value of oxygen concentration in the feed gas, and a target value of carbon dioxide concentration in the feed gas, wherein the target value of the alkylene concentration in the feed gas, the target value of the oxygen concentration in the feed gas, the target value of carbon dioxide concentration in the feed gas, and the desired value of the alkylene oxide production parameter correspond to a first reaction temperature. The method further comprises maintaining the carbon dioxide concentration in the feed gas above its corresponding target value while maintaining the alkylene concentration in the feed gas and the oxygen concentration in the feed gas at or above their corresponding target values to maintain the desired value of the alkylene oxide production parameter at a second reaction temperature greater than the first reaction temperature.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Figure 1:
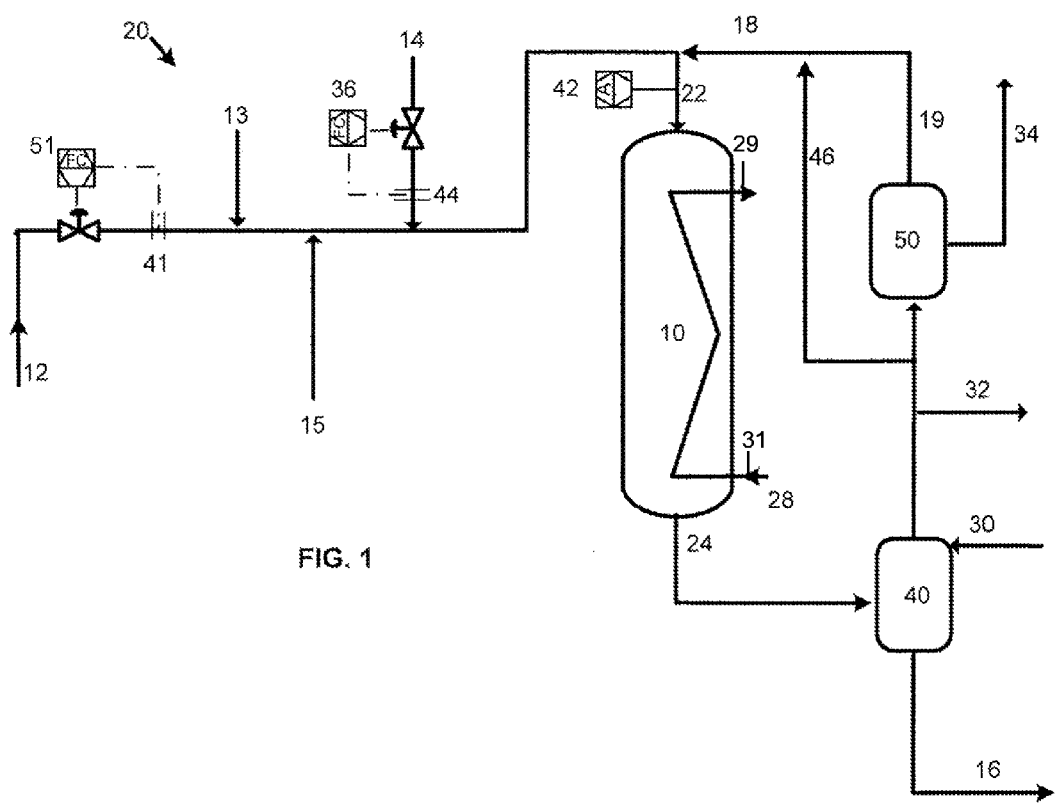
FIG. 1 is a process flow diagram depicting an embodiment of a process for making an alkylene oxide by epoxidizing an olefin over a high efficiency catalyst.

As discussed below, the present disclosure provides a method for reducing the value of an alkylene oxide production parameter while maintaining a substantially maximum efficiency toward the alkylene oxide by reducing at least one process parameter comprising feed gas oxygen concentration in a process of manufacturing an alkylene oxide by reacting an alkylene, oxygen, and at least one organic chloride over a high-efficiency catalyst. In certain embodiments, decreasing oxygen alone will be insufficient to obtain the desired value of the alkylene oxide production parameter. In such cases, the concentration of alkylene in the reactor feed gas and/or reactor pressure may also be reduced, either concurrently with or subsequent to the reduction in oxygen concentration. In other cases, the concentration of carbon dioxide in the feed gas may also be increased above a target value. In certain preferred embodiments, the disclosed techniques allow the alkylene oxide production parameter to be reduced while maintaining the process at or close to an optimum or substantially optimum operating condition. In other preferred embodiments, the methods are carried out after establishing an initial operating condition at which the reactor feed gas oxygen concentration is maintained at a maximum pre-selected value, such as may be dictated by a measure of flammability of the reactor feed gas. The techniques described herein may also be used to maintain a desired value of an alkylene oxide production parameter during the early life of a catalyst when catalyst activity is at its highest and minimum reaction temperature constraints are encountered.

In order to facilitate an understanding of the present disclosure, it is useful to define certain terms relating to catalyst and process performance. The activity of a catalyst in a fixed bed reactor is generally defined as the reaction rate towards the desired product per unit of catalyst volume in the reactor. The activity relates to both the total number of available active sites and the reaction rate of each site. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reaction temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. The "yield" of alkylene oxide refers to the net number of moles of alkylene oxide produced by the process divided by the net number of moles of olefin fed to the process for any given time period.

The term "alkylene oxide production parameter" is used herein to describe a variable that relates to the extent to which alkylene oxides are produced. Examples of alkylene oxide production parameters include, without limitation, alkylene oxide concentration, alkylene oxide yield, alkylene oxide production rate, alkylene oxide production rate/catalyst volume (also known as the alkylene oxide "work rate"), alkylene conversion, and oxygen conversion. The alkylene oxide concentration relates to the alkylene oxide production rate because the production rate may be obtained by multiplying the alkylene oxide concentration and the net product flow rate. Depending on the configuration of the process, an alkylene oxide production rate may be determined at the reactor outlet, downstream of a reactor outlet recycle stream, or downstream of separation processes (e.g., scrubbers) used to extract the alkylene oxide product. As used herein, the term "reaction product" includes unreacted feed components as well as those that are generated as a result of a chemical reaction. In the example of ethylene oxide processes, the "reaction product" would include ethylene oxide, and if present, any by-products (such as carbon dioxide) or unreacted feed components (such has ethylene, oxygen, and/or chlorides). The alkylene oxide production rate/catalyst volume (work rate) may be determined by dividing the production rate by the volume of the catalyst bed. The oxygen and alkylene conversions are related to the production of the alkylene oxide by the efficiency.

FIG. 1 illustrates a process 20 for making an alkylene oxide. Process 20 includes a reactor 10 comprising a tubular vessel with a catalyst bed disposed in it. Olefin (i.e., alkylene) feed stream 12 (which may also include saturated hydrocarbons, such as ethane, as an impurity) is combined with ballast gas 13, oxygen feed 15 and gas phase promoter feed 14 to define reactor feed gas inlet stream 22 proximate the reactor inlet. Reactor product stream 24 includes the alkylene oxide ("AO") product, plus side products (e.g., $CO_2$, $H_2O$, and small amounts of saturated hydrocarbons), unreacted olefin, oxygen, and inerts. Water stream 30 is added to alkylene oxide absorber 40 to absorb alkylene oxide product from reactor product stream 24. Net product stream 16 comprises water and alkylene oxide, and the alkylene oxide is subsequently separated from the water.

If desired, recycle stream 18 may also be provided to reduce the amount of fresh make-up alkylene fed to the reactor 10. One example of a suitable recycle system is depicted in FIG. 1. As shown in the figure, alkylene oxide absorber 40 produces an overhead gas stream comprising unreacted olefin, saturated hydrocarbon impurities or byproducts, and carbon dioxide. Carbon dioxide is removed in $CO_2$ removal unit 50 (e.g., a $CO_2$ scrubber) and exits $CO_2$ removal unit 50 in carbon dioxide stream 34. The overhead stream 19 from unit 50 is combined with $CO_2$ removal unit 50 bypass stream 46 to define recycle stream 18. Recycle stream 18 is combined with olefin feed 12, ballast gas 13, oxygen feed 15, and gas phase promoter feed 14 to define reactor feed stream 22. Purge line 32 is also provided to provide for the removal of saturated hydrocarbon impurities (e.g., ethane), inerts (such as argon), and/or byproducts (as well as carbon dioxide) to prevent their accumulation in reactor feed 22.

The olefin comprising olefin feed stream 12 may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1$=$CH_3$, $R_2$=H) and ethylene ($R_1$=$R_2$=H) are more preferred, and ethylene is most preferred. Correspondingly, preferred alkylene oxides in reactor product stream 24 are of the formula:

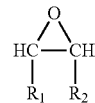

wherein, $R_1$ and $R_2$ are individually selected from the group consisting of hydrogen and alkyl radicals having from 1 to 6 carbon atoms. Propylene oxide ($R_1$=$CH_3$, $R_2$=H) and ethylene oxide ($R_1$=$R_2$=H) are more preferred, and ethylene oxide is most preferred.

Oxygen feed 15 may comprise substantially pure oxygen or air. If pure oxygen is used, ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least one (1) mole percent, preferably at least two (2) mole percent, and still more preferably at least four (4) mole percent. The oxygen concentration will generally be no more than fifteen (15) mole percent, preferably no more than twelve (12) mole percent, and even more preferably no more than nine (9) mole percent. The ballast gas 13 (e.g., nitrogen or methane) is generally from 50 mole percent to 80 mole percent of the total composition of reactor feed stream 22. Methane ballast gas is preferred over nitrogen because, due to its higher heat capacity, it facilitates the use of higher oxygen concentrations in the cycle, and therefore, improves both activity and efficiency.

In certain exemplary processes, the concentration of oxygen in reactor feed 22 is set at a pre-selected maximum value which is no greater than an amount of oxygen that would form a flammable mixture with the components of reactor feed 22 at the prevailing process conditions (the "oxygen flammability concentration"). In other embodiments, the maximum oxygen concentration is no greater than a pre-defined percentage of the oxygen flammability concentration (e.g., the maximum oxygen concentration is no greater than 95% of the oxygen flammability concentration and preferably no greater than 90% of the oxygen flammability concentration). In certain further embodiments, the maximum oxygen concentration and/or the oxygen flammability concentration is determined based on at least one variable selected from the group consisting of reaction temperature, pressure, alkylene concentration, alkylene oxide concentration, ballast gas concentration, and carbon dioxide concentration in reactor feed 22.

The concentration of olefin in reactor feed stream 22 may vary over a wide range. However, it is preferably at least eighteen (18) mole percent and more preferably at least twenty (20) mole percent. The concentration of olefin in reactor feed stream 22 is preferably no greater than 50 mole percent, and more preferably is no greater than 40 mole percent.

The carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than 5 mole percent, preferably no more than 3 mole percent, and even more preferably no more than 2 mole percent of the total composition of reactor feed 22. Water is also a reaction by-product, and may be present in the feed gases in concentrations that are preferably from 0 to no more than three (3) mole percent.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to 2 mole percent. Given the competing effects of the gas phase promoter and the non-halogenated, non-promoting hydrocarbons in reactor feed stream 22, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity $Z^*$ and represented by the following formula:

$$Z^* = \frac{\text{ethyl chloride equivalent } (ppmv)}{\text{ethane equivalent (mole percent)}} \quad (4)$$

wherein the ethyl chloride equivalent is the concentration in ppmv of ethyl chloride that provides substantially the same catalyst chloriding effectiveness of the organic chlorides present in reactor feed stream 22 at the concentrations of the organic chlorides in feed stream 22; and the ethane equivalent is the concentration of ethane in mole percent that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of $Z^*$ would then be 3 ppmv. As a further example, it has been found that for certain catalysts methyl chloride has 10 times less the chloriding effectiveness of ethyl chloride. Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0× (vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (1)) is the concentration of ethane in mole percent in reactor feed stream 22 plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed 22 having 30.0 mole percent ethylene and 0.3 mole percent ethane, the ethane equivalent will then be 0.6 mole percent. As another illustration, it has been found that for certain catalysts methane has 500 times less the dechloriding effectiveness of ethane. Thus, for such catalysts the ethane equivalent for methane is 0.002×

(methane concentration in mol percent). For a hypothetical inlet reactor feed 22 having 30.0 mole percent ethylene and 0.1 mole percent ethane, the ethane equivalent then will be 0.4 mole percent. For an inlet reactor feed 22 having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where reactor feed stream 22 includes ethylene, ethyl chloride, ethylene dichloride, vinyl chloride, and ethane, the overall catalyst chloriding effectiveness value of process 20 can be defined as follows:

$$Z^* = \frac{(ECL + 2*EDC + VCL)}{(C_2H_6 + 0.01*C_2H_4)} \quad (5)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter and the hydrocarbon dechlorinating species also be measured under the reaction conditions which are being used in the process. Z* will preferably be maintained at a level that is no greater than 20 and which is most preferably no greater than 15. Z* is preferably at least 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, and ethylene dichloride must be considered in calculating Z*.

The order in which the inlet gases (alkylene oxide and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics. The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene).

As depicted in FIG. 1, in reactors cooled with boiling water, a countercurrent flow scheme is typically used in which the coolant is introduced as liquid water to the cooling side (most commonly the shell side) of reactor 10 at coolant side inlet 31 proximate the process outlet 24 of reactor 10. As it flows through the cooling side, the water removes heat from the process side, and some of the water is vaporized to steam. The coolant exits the cooling side of the reactor at cooling side outlet 29 proximate process side inlet 22 as a mixture of water and steam. The steam exiting the reactor is condensed by removing heat from it, and is recycled back to the inlet 28 of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature. The epoxidation reaction is carried out at a temperature that is preferably at least 200° C., more preferably at least 210° C., and most preferably at least 220° C. Reaction temperatures of no more than 300° C. are preferred, and reaction temperatures of no more than 290° C. are more preferred. Reaction temperatures of no more than 280° C. are most preferred. The reactor pressure is selected based on the desired mass velocity and productivity and ranges generally from 5 atm (506 kPa) to 30 atm (3.0 MPa). The gas hourly space velocity (GHSV) is preferably greater than 3000 $h^{-1}$, more preferably greater than 4,000 $hr^{-1}$, and most preferably greater than 5,000 $hr^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least 80 weight percent α-alumina and less than 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least 0.5 $m^2/g$, and more preferably, at least 0.7 $m^2/g$. The surface area is typically less than 10 $m^2/g$, and preferably, less than 5 $m^2/g$. The alpha-alumina carrier preferably has a pore volume of at least 0.3 $cm^3/g$, and more preferably, from 0.4 $cm^3/g$ to 1.0 $cm^3/g$ and a median pore diameter from 1 to 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than 50 microns. In a preferred embodiment, the alpha-alumina carrier comprises zirconium silicate (zircon), present substantially as zirconium silicate in the finished carrier, more preferably, in an amount up to 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Typically, the amount of silver supported on the carrier is less than 70 percent, and more preferably, less than 50 percent by weight, based on the weight of the catalyst.

Although silver particle size in the finished catalyst is important, the range is not narrow. A suitable silver particle size can be in the range of from 10 to 10,000 angstroms in diameter. A preferred silver particle size ranges from greater than 100 to less than 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature.

The concentration of alkali metal (based on the weight of cation, for example cesium) in the finished catalyst may vary from 0.0005 to 1.0 wt. %, preferably from 0.005 to 0.5 wt. %. The preferred amount of cation promoter deposited on or present on the surface of the carrier or catalyst generally lies between 10 and 4000, preferably 15 and 3000, and more preferably between 20 and 2500 ppm by weight of cation calculated on the total carrier material. Cation promoter amounts between 50 and 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from 0.0001:1 to 10,000:1, preferably from 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $[Sa_4]^{-2}$, phosphates, for example, $[PO_4]^{-3}$, titanates, e.g., $[TiO_3]^{-2}$, tantalates, for example, $[Ta_2O_6]^{-2}$, molybdates, for example, $[MoO_4]^{-2}$, vanadates, for example, $[V_2O_4]^{-2}$, chromates, for example, $[CrO_4]^{-2}$, zirconates, for example, $[ZrO_3]^{-2}$, polyphosphates, manganates, nitrates, chlorates, bromates, borates, silicates, carbonates, tungstates, thiosulfates, cerates, rheanates, perrhenates, and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $[MoO_4]^{-2}$, and $[Mo_7O_{24}]^{-6}$ and $[Mo_2O_7]^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylene-diamine-tetraacetic acid (EDTA) or a suitable salt thereof.

The amount of anion promoter may vary widely, for example, from 0.0005 to 2 wt. %, preferably from 0.001 to 0.5 wt. % based on the total weight of the catalyst. When used, the rhenium component is often provided in an amount of at least 1, say, at least 5, for example, 10 to 2000, often between 20 and 1000, ppmw calculated as the weight of rhenium based on the total weight of the catalyst.

It is desirable that the silver and one or more solid promoters be relatively uniformly dispersed on the carrier. Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

As is known in the art, the yield of alkylene oxide depends on the rate of olefin consumption, and the rates of competing side reactions. With conventional catalysts, a desired rate of alkylene oxide production can be achieved by varying reaction temperature without sacrificing efficiency substantially. However, with high efficiency catalysts, efficiency is typically dependent on both the overall catalyst chloriding effectiveness and the reaction temperature. Thus, a change that would increase the rate of olefin consumption may be accompanied by a corresponding decrease in efficiency. It is generally desirable to maximize efficiency to minimize the raw material consumption and the generation of unwanted byproducts (carbon dioxide and water). Because efficiency varies with both overall catalyst chloriding effectiveness and reaction temperature, both variables must typically be varied in order to obtain a desired alkylene oxide production parameter. It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet coolant temperature or outlet temperature.

Given the relationships between reaction temperature, Z* and efficiency for a high efficiency catalyst, using either variable to reduce the value of an alkylene oxide production parameter may be undesirable. If the reaction temperature is decreased significantly in a short time, the optimum chloriding level of the catalyst may not be maintained even if Z* is adjusted properly and promptly because it may take a high-efficiency catalyst several days to reach steady state following a change in Z*. In certain cases, Z* is not manipulable with sufficient sensitivity to control an alkylene oxide production parameter due to limitations in the ability to tightly measure and control the flow rate of gas phase promoters. In addition, the use of Z* to control an alkylene oxide parameter can lead to operation at Z* values which in some circumstances may cause irreversible damage to the catalyst.

It has been discovered that variables other than reaction temperature and overall chloriding effectiveness may be changed in a manner that reduces the rate of alkylene and oxygen consumption without causing the process to deviate significantly from an optimum or substantially optimum efficiency. As a result, an alkylene oxide production parameter may be reduced from an initial value without sacrificing efficiency. The variables that may be used to reduce the value of an alkylene oxide production parameter in accordance with the methods described herein include feed gas oxygen concentration (or partial pressure), feed gas alkylene concentration (or partial pressure), reactor feed gas inlet pressure, and carbon dioxide concentration (or partial pressure).

Figure 2:
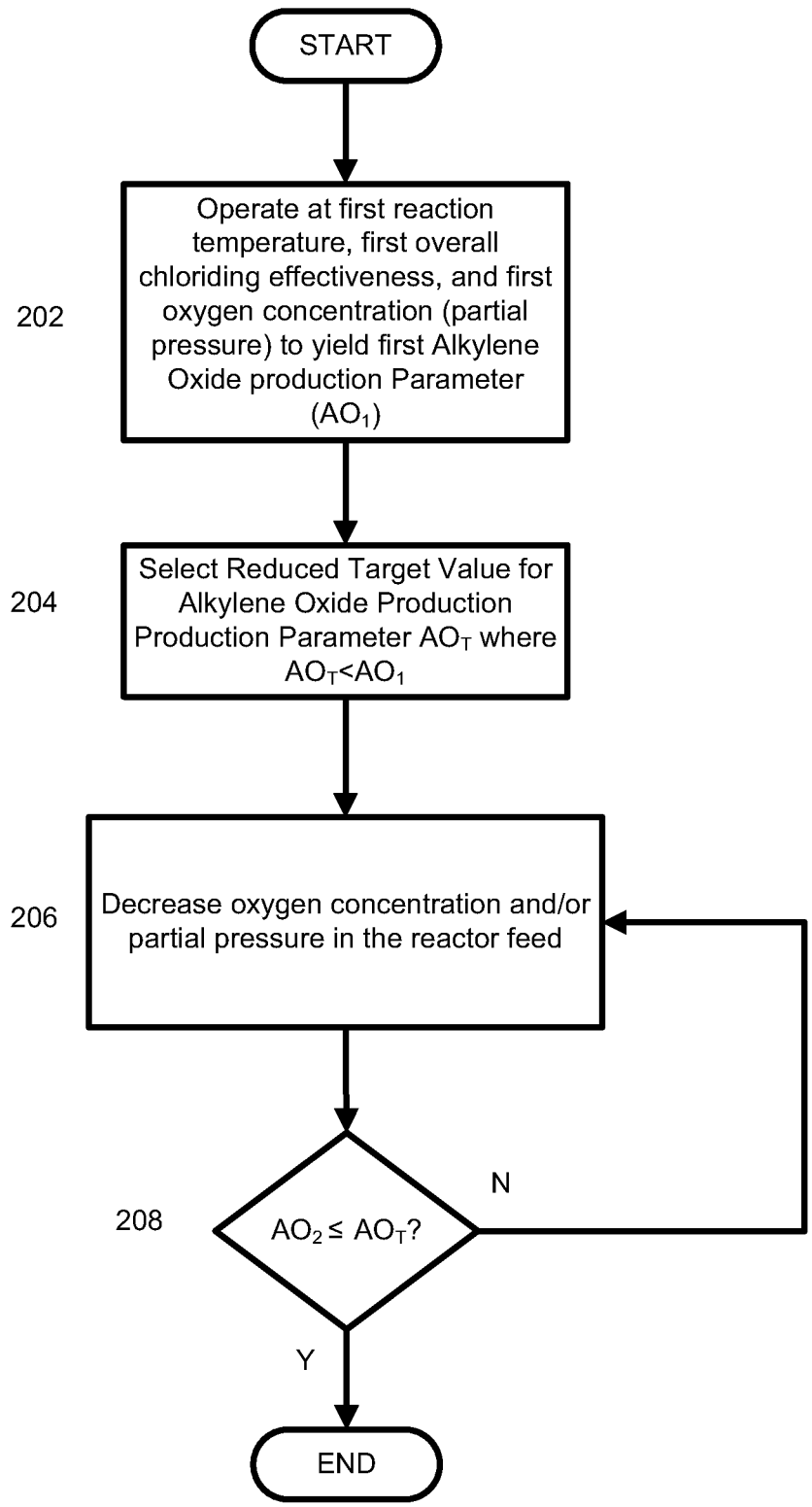
FIG. 2 is a flow chart depicting a first embodiment of a method for reducing the value of an alkylene oxide production parameter in the process of FIG. 1.

Referring to FIG. 2, a method of reducing the value of an alkylene oxide production parameter will now be described. In accordance with the method, in step 202 process 20 is operated at an initial operating condition comprising a first reaction temperature, a first overall chloriding effectiveness, a first oxygen concentration, a first alkylene concentration, and a first reaction pressure to yield a first value of the alkylene oxide production parameter ($AO_1$). As is known to those skilled in the art, the partial pressures of gas components may be calculated by multiplying the molar fractions of the components by the total absolute pressure. Thus, the first concentration of oxygen and the first reactor feed gas inlet pressure will define and correspond to a first oxygen partial pressure. Similarly, the first concentration of the alkylene and the first reactor feed gas inlet pressure will define and correspond to a first alkylene partial pressure. A variety of methods may be used to select the initial operating condition used in step 202, several of which will be described below. In certain preferred embodiments, the initial operating condition will comprise an optimum or substantially optimum operating condition. In other preferred embodiments, the concentration of oxygen in the feed gas at the initial operating condition will be a pre-selected maximum concentration. In certain examples, the pre-selected maximum oxygen concentration will be based on the oxygen flammability concentration. Pre-selected maximum molar oxygen concentrations (in mole percent) of no greater than 0.95 and 0.90 of the oxygen flammability concentration are preferred and more preferred, respectively. In step 204, a reduced target value ($AO_T$) for the alkylene oxide production parameter is selected. In one example, a downstream unit such as an alkylene glycol unit may develop a bottleneck which reduces the amount of alkylene oxide it can receive. In such a case, it may be desirable to reduce the rate of alkylene oxide production from process 20. In other examples, market conditions may dictate a reduction in the rate of production of the alkylene oxide.

It has been discovered that the concentration of oxygen in the reactor feed gas 22 can be decreased to achieve a reduced target alkylene oxide production parameter value without significantly deviating from an optimum operating condition. The change in the oxygen concentration will preferably yield a new value for the alkylene oxide production parameter $AO_2$, which is less than the first value of the parameter, $AO_1$. Thus, in step 206 the concentration of oxygen in the reactor inlet feed gas stream 22 is decreased by a selected amount. The reduction in the oxygen concentration may be carried out in a number of ways, including one or more step changes, one or more ramp changes, one or more non-linear changes, and various combinations of step, ramp, and non-linear changes. In one example, the flow rate of oxygen feed gas stream 15 is reduced (or the flow rate of an air stream is reduced in processes that use air for the epoxidation). The concentration of oxygen is preferably reduced while maintaining the overall chloriding effectiveness at substantially the first overall chloriding effectiveness value established in step 202. During step 206, the partial pressure of oxygen is also preferably reduced, such as would be the case if the concentration of oxygen were reduced while the reactor pressure was held constant or decreased.

In certain exemplary embodiments, the reduction in feed gas oxygen concentration is carried out with the reaction temperature controller in open loop so that the temperature can be used to indicate the effect of the oxygen reduction on the optimum operation of process 20. In accordance with such examples, the reduction in feed gas oxygen concentration in step 206 yields a temperature decrease that is no greater than a pre-selected maximum amount. The pre-selected maximum decrease is preferably no greater than 4° C., more preferably no greater than 3° C., and even more preferably no greater than 2° C. In other examples, the oxygen concentration in reactor feed 22 is preferably reduced to no less than one (1) mole percent, more preferably to no less than two (2) mole percent, and still more preferably to no less than four (4) mole percent. In additional examples, the reduction in the oxygen concentration yields an oxygen partial pressure that is preferably no less than 7 kPa, more preferably no less than 14 kPa, and still more preferably no less than 30 kPa.

In step 208 the new parameter value $AO_2$ is compared to the target value $AO_T$. If the new parameter value is less than or equal to the target value, the process is terminated. If not, the concentration of oxygen is further reduced until the target value $AO_T$ is reached. However, the concentration of oxygen in the reactor feed gas 22 is preferably not reduced below the values above. If it becomes desirable to do so, the alkylene oxide production parameter can later be raised back to $AO_1$ by raising the concentration of oxygen in reactor feed gas 22, subject to any intervening process changes which may have altered the maximum desirable oxygen concentration.

In certain preferred examples, the reduction in the concentration of oxygen in step 206 yields an efficiency to the alkylene oxide that deviates from an optimum (or substantially optimum) efficiency (at the reduced oxygen concentration) by no more than preferably 1.0 percent, more preferably 0.8 percent, and even more preferably 0.5 percent. The optimum efficiency may be determined in a variety of different ways. In certain examples, the optimum efficiency is based on the combination of the alkylene oxide production parameter, reaction temperature, and overall chloriding effectiveness. In one exemplary scenario, the optimum efficiency is the maximum efficiency attainable based on the minimum attainable reaction temperature and the corresponding overall chloriding effectiveness that provides the maximum efficiency at the minimum attainable reaction temperature. The minimum attainable temperature will be dictated by the heat transfer constraints imposed by the reactor coolant system. In other examples, the optimum efficiency is the maximum efficiency obtainable at the resulting alkylene oxide production parameter $AO_2$ by varying the overall chloriding effectiveness (e.g., $Z^*$) at a constant concentration of the alkylene in the feed gas and a fixed process condition. In still other examples, at the fixed process condition, at least one of reactor feed gas inlet pressure, feed gas oxygen concentration, feed gas carbon dioxide concentration, and gas hourly space velocity is held constant. In further examples, each of these variables is held constant in determining the optimum efficiency as the overall chloriding effectiveness is varied.

Referring to FIG. 2, in certain cases, the reduction in feed gas oxygen concentration and/or partial pressure may be insufficient to reach the reduced alkylene oxide production parameter target value, $AO_T$. Thus, in a modified version of the method of FIG. 2, after reducing the feed gas concentration and/or partial pressure of oxygen in step 206, the feed gas concentration of alkylene is reduced to reach the target value $AO_T$.

The reduction in the alkylene concentration is preferably accompanied by a reduction in the feed gas alkylene partial pressure. The reduction in feed gas alkylene concentration is preferably carried out while maintaining a substantially constant value of the overall chloriding effectiveness. However, the alkylene concentration affects the overall chloriding effectiveness value. Thus, a compensating change is typically made to offset the change in the overall chloriding effectiveness which would otherwise result from decreasing the feed gas concentration of the alkylene. As indicated by the formula for $Z^*$ described above, a reduction in alkylene concentration will cause the overall chloriding effectiveness to increase. In one example, the concentration of the at least one organic chloride in the feed gas is reduced in a manner that offsets the effect of reducing the alkylene concentration. After reducing the feed gas alkylene concentration, the resulting alkylene oxide production parameter value $AO_2$ is compared to the target value $AO_T$. If the new value $AO_2$ is less than or equal to the target value $AO_T$, the process is terminated. Otherwise, the concentration of alkylene is further reduced.

In certain preferred embodiments, the concentration of alkylene in the reactor feed gas 22 is reduced to no lower than a pre-selected value. The pre-selected value is preferably at least 15 mole percent, more preferably at least 18 mole percent, and even more preferably at least 20 mole percent. The reduction in the alkylene concentration may be carried out in a number of ways, including one or more step changes, one or more ramp changes, one or more non-linear changes, and various combinations of step, ramp, and non-linear changes. In certain embodiments, the reduction in alkylene concentration is corresponds to a reduced partial pressure that is at preferably at least 97 kPa psia, more preferably at least 117 kPa, and even more preferably at least 131 kPa.

In certain preferred examples, the reduction in the concentration of the alkylene yields an efficiency to the alkylene oxide that deviates from an optimum (or substantially optimum) efficiency (at the reduced alkylene concentration) by no more than preferably 1.0 percent, more preferably, 0.8 percent, and even more preferably 0.5 percent. The optimum efficiency may be determined in a variety of different ways, including those described above with respect to FIG. 2 and additional methods discussed further below.

In certain cases, reducing feed gas oxygen and alkylene concentrations may prove insufficient to reach the reduced target value of the alkylene oxide production parameter, $AO_T$. Thus, in a further modified version of the method of FIG. 2, after the feed gas oxygen and feed gas alkylene concentrations are reduced, the reactor inlet feed gas pressure is decreased. For example, in certain commercial plants, a recycle gas compressor is provided with a discharge pressure controller, and the set point of the pressure controller may be reduced. The pressure reduction may be carried out in a variety of ways, including one or more step changes, one or more ramp changes, one or more non-linear changes, and various combinations of step, ramp, and non-linear changes. In certain preferred examples, the reduction in feed gas pressure is carried out while maintaining the overall chloriding effectiveness at substantially the first overall chloriding effectiveness value established in step 202. The reduction in pressure will decrease the respective partial pressures of oxygen and the alkylene in the feed. However, in certain preferred examples their respective molar concentrations are held substantially constant during while reducing feed gas pressure. The resulting alkylene oxide production parameter value $AO_2$ is compared to the target value $AO_T$. If the resulting parameter value $AO_2$ is less than or equal to the target value $AO_T$, the process is terminated. Otherwise, the reactor inlet feed gas pressure is further reduced.

In certain illustrative embodiments, the reactor inlet feed gas pressure is preferably reduced to no less than a pre-selected minimum value. In certain examples, the pre-selected minimum value is no less than 650 kPa, more preferably no less than 720 kPa, and even more preferably no less than 790 kPa. In other examples, the reactor inlet feed gas pressure is reduced by no more than a pre-selected amount (i.e., a maximum $\Delta P$) during step 206. The pre-selected maximum pressure decrease is preferably no greater than 550 kPa, more preferably no greater than 480 kPa, and even more preferably no greater than 415 kPa. The minimum pressure is typically dictated by the design and operability of the equipment in the cycle loop.

In certain preferred examples, the reduction in the reactor inlet 22 feed gas pressure yields an efficiency to the alkylene oxide that deviates from an optimum (or substantially optimum) efficiency by no more than 1.0 percent, more preferably 0.8 percent, and even more preferably 0.5 percent. The optimum efficiency may be determined in a variety of different ways, including those described above with respect to FIG. 2 and those described below. In additional implementations, it may eventually be desirable to increase the alkylene oxide production parameter value. In one example, this is carried out by reversing the sequence of operations used to decrease the alkylene oxide parameter value, e.g., by first increasing feed gas pressure, then increasing the feed gas alkylene concentration, and then increasing the feed gas oxygen concentration.

In some cases, it may not be possible or desirable to achieve the reduced target value of the alkylene oxide production parameter by reducing feed gas oxygen concentration, feed gas alkylene concentration, and feed gas pressure alone. Thus, in a further modified version of the method of FIG. 2, following the reduction of these three variables the concentration of carbon dioxide in the reactor inlet 22 feed gas is increased, preferably causing the alkylene oxide production parameter to decrease. The partial pressure of carbon dioxide in the reactor inlet 22 feed gas preferably increases as a result. The alkylene oxide production parameter $A_{O2}$ is compared to the target value $A_{OT}$. If the resulting parameter value $A_{O2}$ is less than or equal to the target value $A_{OT}$, the process is terminated. Otherwise, the carbon dioxide pressure is further increased. In additional implementations, it may eventually be desirable to increase the alkylene oxide production parameter value. In one example, this is carried out by reversing the sequence of operations used to decrease the alkylene oxide parameter value, e.g., by first decreasing the feed gas carbon dioxide concentration, then increasing feed gas pressure, then increasing the feed gas alkylene concentration, and then increasing the feed gas oxygen concentration.

Referring to FIG. 1, the carbon dioxide concentration (and partial pressure) in the reactor feed gas inlet 22 can be increased in a number of ways. In one method, the carbon dioxide removal unit bypass line 46 flow rate is increased to route more of the total recycled gas around the removal unit 50. In another method, the process conditions used in carbon dioxide removal unit 50 are modified to remove less carbon dioxide from the recycle gas, thus decreasing the flow rate of carbon dioxide stream 34. In examples wherein carbon dioxide removal unit 50 is a scrubber, the flow rate of the scrubbing medium (e.g., amine, NaOH) can be decreased to decrease carbon dioxide removal. In addition, the pressure of the scrubber can be decreased and/or its temperature can be increased to disfavor absorption of carbon dioxide in the scrubbing medium. In certain examples, the amount of carbon dioxide supplied via recycle stream 18 may be decreased to offset an increase in the carbon dioxide content of the fresh alkylene feed stream 12 or any other feed stream without increasing the concentration of carbon dioxide in reactor inlet feed stream 22 and thereby avoiding a decrease in the efficiency of the process to the alkylene oxide.

In certain preferred examples, the increase in the reactor inlet 22 feed gas carbon dioxide concentration yields an efficiency to the alkylene oxide that deviates from an optimum (or substantially optimum) efficiency by no more than preferably 1.0 percent, more preferably 0.8 percent, and even more preferably 0.5 percent. The optimum (or substantially optimum) efficiency may be determined in a variety of different ways, including those described above with respect to FIG. 2 and those described below.

As indicated by the foregoing discussion of FIG. 2 and the above-described variants thereof, in certain exemplary embodiments at least one process parameter selected from the group consisting of feed gas oxygen concentration, feed gas alkylene concentration, reactor inlet pressure, and feed gas carbon dioxide concentration and combinations thereof can be used to reduce the value of an alkylene oxide production parameter. Moreover, the process parameters may be varied sequentially or simultaneously. In addition, different combinations of the process parameters may be varied simultaneously and sequentially. For example, feed gas oxygen concentration and alkylene concentration may be reduced simultaneously or substantially simultaneously followed by a reduction in feed gas pressure and/or feed gas carbon dioxide concentration.

Figure 3:
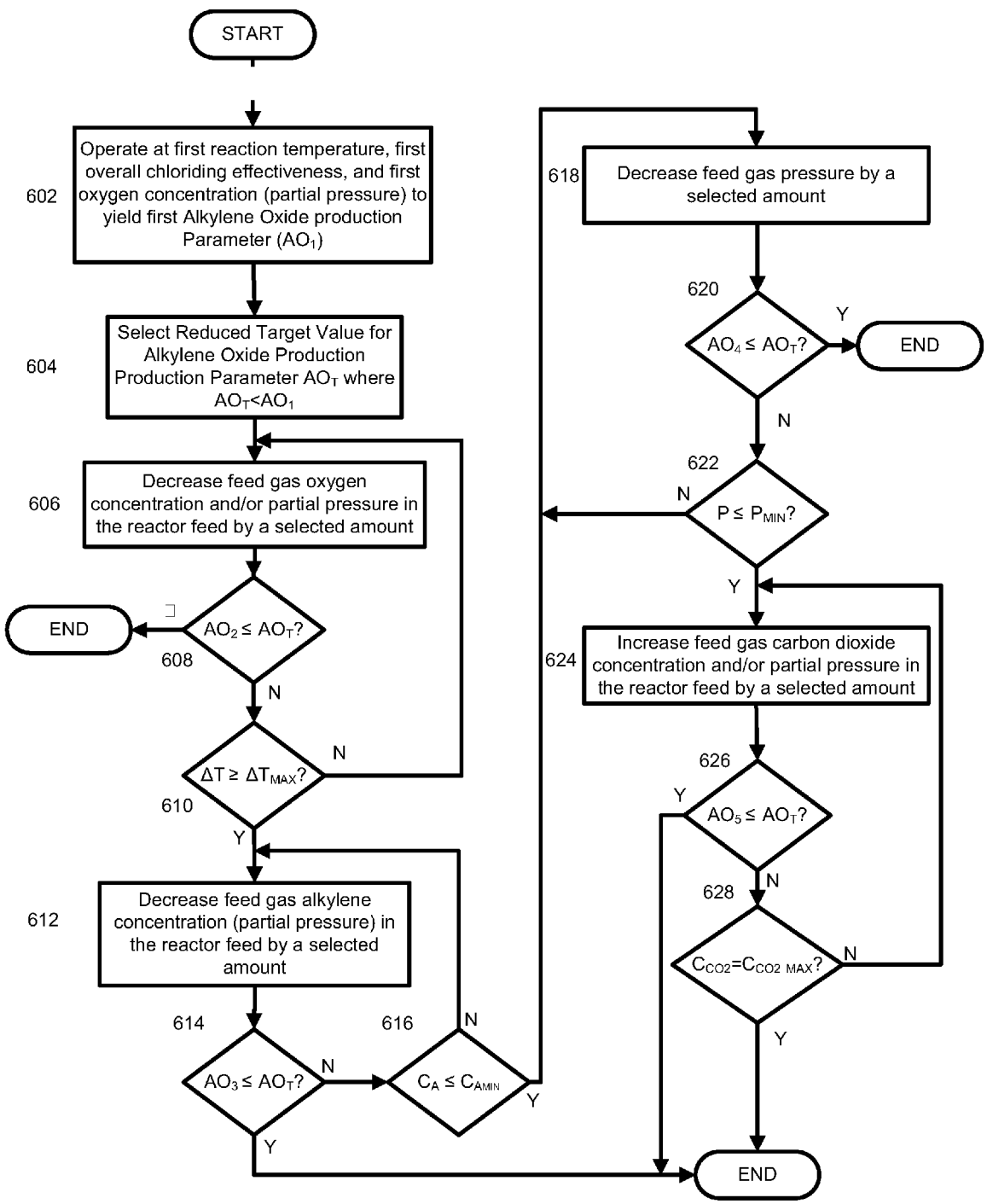
FIG. 3 is a flow chart depicting a second embodiment of a method for reducing the value of an alkylene oxide production parameter in the process of FIG. 1.

One preferred exemplary technique for reducing the value of an alkylene oxide production parameter in accordance with the methods disclosed herein is depicted in FIG. 3. In accordance with the method, an initial operating condition is selected in step 602 in the manner described previously with respect to step 202, yielding an initial alkylene oxide production parameter value $AO_1$. In step 604, a target value $AO_T$ of the alkylene oxide production parameter is selected, wherein the target value $AO_T$ is less than the initial value $AO_1$. In step 606, the concentration of oxygen in the reactor feed gas inlet 22 is decreased in the manner described previously for step 206. The reduction in feed gas oxygen concentration preferably yields a reduction in the alkylene oxide production parameter from its initial value $AO_1$ to a new value $AO_2$. In addition, the reduction in feed gas oxygen concentration is preferably accompanied by a corresponding reduction in the partial pressure of oxygen in reactor feed gas inlet 22.

Figure 6A:
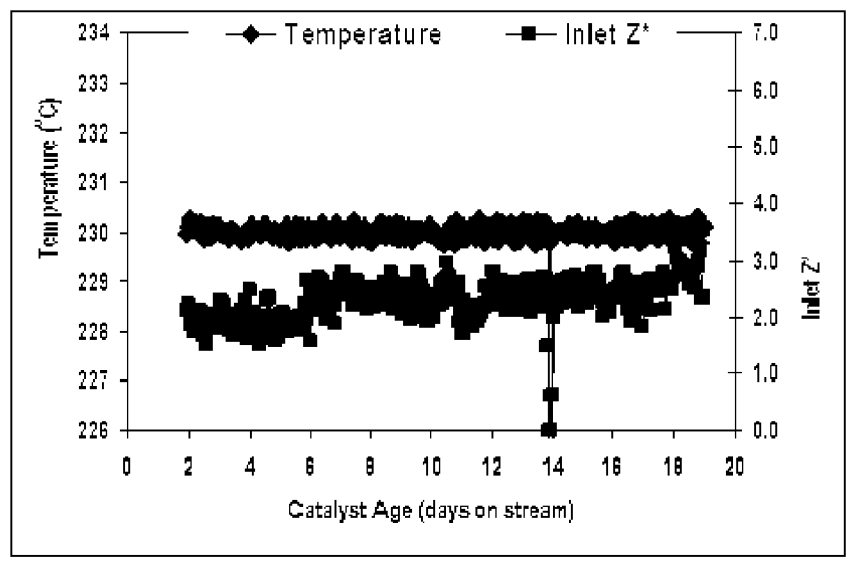
FIG. 6A is a graph depicting reaction temperature and overall chloriding effectiveness used to illustrate an exemplary method of reducing ethylene oxide concentration by reducing feed gas oxygen concentration in a process for producing ethylene oxide using a high-efficiency catalyst.
Figure 6B:
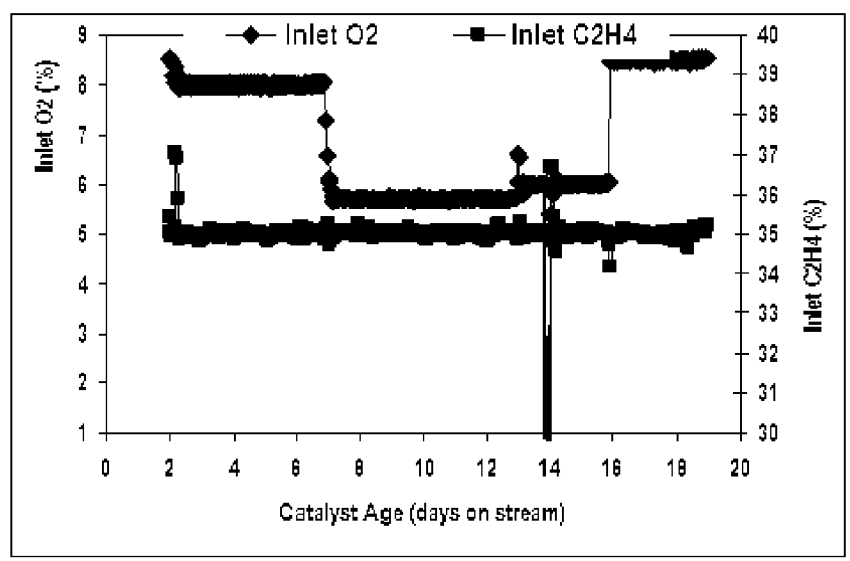
FIG. 6B is a graph depicting feed gas oxygen concentration and feed gas ethylene concentration used to illustrate the exemplary method of FIG. 6A.

In step 608, the new value $AO_2$ of the alkylene oxide production parameter is compared to the target value $AO_T$. If the new value $AO_2$ is less than or substantially equal to the target value $AO_T$, the process is terminated. However, if $AO_2$ is greater than $AO_T$, an efficiency-indicating parameter is used to determine whether any further decreases in oxygen concentration may cause an undesirable decline in the efficiency to the alkylene oxide. One such efficiency-indicating parameter is reaction temperature. In one method wherein step 606 is conducted without controlling the reaction temperature to a specified set-point (i.e., with the temperature controller set on manual or in "open loop"), the reaction temperature change resulting from the decrease in feed gas oxygen concentration is monitored, and the reduction in oxygen concentration is manipulated to maintain a pre-selected maximum temperature decrease. An example of such a method is depicted in step 610 of FIG. 6. As indicated in the figure, the reaction temperature decrease $\Delta T$ is monitored and is compared to the pre-selected maximum temperature decrease $\Delta T_{max}$. If the reaction temperature decrease $\Delta T$ is less than the pre-selected maximum temperature decrease $\Delta T_{max}$, the method returns to step 604. However, if the reaction temperature decrease $\Delta T$ is greater than or substantially equal to the pre-selected maximum temperature decrease $\Delta T_{max}$, the method proceeds to step 612. The value of $\Delta T_{max}$ is preferably 4° C., more preferably 3° C., and even more preferably 2° C. In certain preferred examples, step 606 is carried out while maintaining the overall chloriding effectiveness of the process at a substantially constant value.

In certain preferred examples, the reduction in the concentration of oxygen in step 606 yields an efficiency to the alkylene oxide that deviates from an optimum (or substantially optimum) efficiency by no more than 1.0 percent, more preferably 0.8 percent, and even more preferably 0.5 percent. The optimum or substantially optimum efficiency may be determined in a variety of different ways, including those described above with respect to FIG. 2 and below.

In step 612, the concentration of alkylene in the reactor feed gas inlet 22 is decreased in the same manner as described previously. The reduction is preferably accompanied by a corresponding reduction in the partial pressure of the alkylene in the reactor feed gas inlet 22. As a result of the reduction in the feed gas alkylene concentration, the alkylene oxide production parameter preferably decreases from its previous value $AO_2$ to a new value $AO_3$. In step 614, the new alkylene oxide production parameter value $AO_3$ is compared to the target value $AO_T$. If $AO_3$ is less than or substantially equal to $AO_T$, the method is terminated. Otherwise, the method proceeds to step 616 in which the concentration of the alkylene $C_A$ is compared to a pre-selected minimum alkylene concentration $C_{AMIN}$. If the alkylene concentration $C_A$ is less than or substantially equal to the pre-selected minimum concentration $C_{AMIN}$, the method proceeds to step 618. Otherwise, the method returns to step 612, and the reactor feed gas alkylene concentration is further reduced. In certain preferred examples, step 612 is carried out while maintaining the overall chloriding effectiveness of the process at a substantially constant value. The pre-selected minimum alkylene feed gas concentration value $C_{AMIN}$ is preferably at least 15 mole percent, more preferably, at least 18 mole percent, and even more preferably at least 20 mole percent.

In certain preferred examples, the reduction in the concentration of the alkylene in step 612 yields an efficiency to the alkylene oxide that deviates from an optimum (or substantially optimum) efficiency by no more than preferably 1.0 percent, more preferably 0.8 percent, and even more preferably 0.5 percent. The optimum or substantially optimum efficiency may be determined in a variety of different ways, including those described above with respect to FIG. 2 and below.

In step 618, the feed gas pressure is reduced by a selected amount, preferably resulting in a reduction in the alkylene oxide production parameter value from its previous value $AO_3$ to a new value $AO_4$. In step 620, the new value $AO_4$ is compared to the target value $AO_T$. If the new value $AO_4$ is less than or substantially equal to the target value $AO_T$, the method is terminated. Otherwise, the method proceeds to step 622.

In step 622, the feed gas pressure P is compared to a pre-selected minimum feed gas pressure $P_{MIN}$. In certain examples, the pre-selected minimum value is no less than 650 kPa, more preferably no less than 720 kPa, and even more preferably no less than 790 kPa. In other examples, the reactor inlet feed gas pressure is reduced by no more than a pre-selected amount (i.e., a maximum $\Delta P$) during step 618. The pre-selected maximum pressure decrease is preferably no greater than 550 kPa, more preferably no greater than 480 kPa, and even more preferably no greater than 415 kPa. In step 622, if the feed gas pressure P is less than or substantially equal to the pre-selected minimum pressure $P_{MIN}$ (or if the pressure decrease $\Delta P$ exceeds the pre-selected maximum decrease $\Delta P_{MIN}$), the method proceeds to step 624. Otherwise, the method returns to step 618 and the pressure is further reduced.

In certain preferred examples, the reduction in the reactor inlet 22 feed gas pressure in step 618 yields an efficiency to the alkylene oxide that deviates from an optimum (or substantially optimum) efficiency by no more than preferably 1.0 percent, more preferably 0.8 percent, and even more preferably 0.5 percent. The optimum or substantially optimum efficiency may be determined in a variety of different ways, including those described above with respect to FIG. 2 and below. In certain preferred examples, step 618 is carried out while maintaining the overall chloriding effectiveness of the process at a substantially constant value.

In step 624, the concentration of carbon dioxide in the reactor feed gas inlet 22 is increased by a selected amount in the manner described previously with respect to step 512. The increase in carbon dioxide content preferably reduces the alkylene oxide production parameter from its previous value $AO_4$ to a new value $AO_5$. The increase in carbon dioxide concentration is preferably accompanied by a corresponding increase in the partial pressure of carbon dioxide in reactor feed as inlet 22. In certain examples, the concentration of carbon dioxide is increased while maintaining the overall chloriding effectiveness at a substantially constant value.

In step 626, the new alkylene oxide production parameter $AO_5$ is compared to the target value $AO_T$. If the new value $AO_5$ is less than or equal to the target value $AO_T$, the method is terminated. Otherwise, the method proceeds to step 628. In step 628, the concentration of carbon dioxide in the reactor feed gas inlet 22 is determined. If the concentration is substantially at its maximum ($C_{CO2MAX}$), the method is terminated. Otherwise, the method returns to step 624 and the carbon dioxide concentration is further increased. In certain preferred examples, the increase in the reactor inlet 22 feed gas carbon dioxide concentration in step 624 yields an efficiency to the alkylene oxide that deviates from an optimum efficiency by no more than preferably 1.0 percent, more preferably 0.8 percent, and even more preferably 0.5 percent. The optimum or substantially optimum efficiency may be determined in a variety of different ways, including those described above with respect to FIG. 2 and below. In certain examples, $C_{CO2MAX}$ is preferably no greater than ten (10) mole percent, more preferably no greater than eight (8) mole percent, and even more preferably no greater than six (6) mole percent of the total feed gas composition.

In additional implementations, it may eventually be desirable to increase the alkylene oxide production parameter value. In one example, this is carried out by reversing the sequence of operations used to decrease the alkylene oxide parameter value, e.g., by first increasing feed gas pressure, then increasing the feed gas alkylene concentration, and then increasing the feed gas oxygen concentration.

As mentioned previously, both alkylene oxide concentration and alkylene oxide production rate may be used as an alkylene oxide production parameter in the methods described herein. If a target production (mass flow) rate $F_{AOT}$ is selected, the corresponding concentration $C_{AOT}$ may be calculated from the target mass flow rate, $F_{AOT}$ and the total reactor inlet volumetric flow rate (V) at standard temperature and pressure (273.15° K, 1 atm). In accordance with one method, the change in alkylene oxide concentration as a mole percentage (ΔAO %) is first calculated as follows:

$$\Delta AO\% = (F_{AOT}/MW_{AO})(RT/P)(100/V) \quad (3)$$

wherein $MW_{AO}$ is the molecular weight of the alkylene oxide (e.g., 44.05 g/gmol for ethylene oxide). Based on ΔAO % and the reactor inlet concentration of the alkylene oxide ($C_{AO\ Inlet}$), the following two equations are then simultaneously solved to obtain the outlet concentration of alkylene oxide in mole percent ($C_{AO1}$):

$$\text{Shrink Factor(SF)} = (200 + C_{AO\ Inlet})/(200 + C_{AOT}). \quad (4)$$

$$\Delta AO\% = SF*C_{AOT} - C_{AO\ Inlet} \quad (5)$$

The "Shrink Factor" represents the net volumetric reduction occurring due to the production of the alkylene oxide. For example, in the case of ethylene oxide production, for every mole of ethylene oxide produced, there is a net reduction of 0.5 moles of total gas resulting in a corresponding reduction in the volumetric flow rate.

The method of FIG. 2 and the above-described variants thereof all involve the selection of an initial operating condition and the manipulation of at least one process parameter to reduce the value of an alkylene oxide production parameter. As mentioned previously, in certain preferred examples, the manipulation of the at least one process parameter results in a deviation of the process from an optimum efficiency by no more than certain specified amounts. Several optimization methods may be used, including those described above with respect to FIG. 2. However, additional methods of defining an optimum (or substantially optimum) condition for purposes of establishing the initial operating condition and/or for evaluating the impact of the process parameter manipulations may be used and will now be described. The methods are not themselves optimization techniques. However, it has been discovered that in certain embodiments, these methods can be used to identify an optimum or substantially optimum operating condition and the corresponding efficiency to the alkylene oxide.

In one embodiment, an optimum or substantially optimum operating condition is defined by selecting the process parameters to maintain the first derivative of efficiency with respect to reactor outlet alkylene oxide concentration at constant temperature, reactor inlet alkylene oxide concentration, and a fixed process condition ($\partial E/\partial C_{AO}$) within a specified range. The fixed process condition is one in which at least one variable selected from the group consisting of pressure, reactor inlet oxygen concentration, reactor inlet carbon dioxide concentration, and gas hourly space velocity is held at a constant value. In one preferred embodiment, the fixed process condition is a condition at which each of pressure, reactor inlet oxygen concentration, reactor inlet carbon dioxide concentration and gas hourly space velocity is held constant.

In another embodiment, the preferred optimum operating condition is one that provides a reactor outlet alkylene oxide concentration ($C_{AO}$) that is higher than the efficiency-maximizing alkylene oxide concentration at an epoxidation temperature. In still another embodiment, the preferred optimum operating condition is selected to provide an overall chloriding effectiveness value that is higher than the efficiency-maximizing overall chloriding effectiveness value. In yet another embodiment, the optimum overall catalyst chloriding effectiveness value $Z_1^*$ and the initial reaction temperature $T_1$ are selected to maximize efficiency toward the alkylene oxide at the desired reactor outlet alkylene oxide concentration, $C_{AO1}$.

Other optimization methods and other methods of determining an optimum operating condition may also be used. For example, it may be desired to operate process 20 at the maximum catalyst efficiency for a given selected initial reaction temperature $T_1$ regardless of the alkylene oxide concentration in the reactor outlet 24. In addition, an efficiency maximizing scheme may be chosen by operating at the minimum obtainable reaction temperature (based on the capacity of coolant circuit 28) and by selecting the value of $Z_1^*$ that obtains the maximum efficiency. Alternatively, reactor outlet alkylene oxide concentration may be maximized regardless of the efficiency (as limited by the maximum temperature the reactor can withstand).

In certain exemplary implementations of the method of FIG. 2 and the above-described variants thereof, the efficiency to the alkylene oxide is substantially stable following the adjustment of the at least one process parameter comprising feed gas oxygen concentration. In accordance with such exemplary implementations, the efficiency preferably varies by no more than 0.8 percent per day, more preferably by no more than 0.5 percent per day, and still more preferably by no more than 0.3 percent per day following the adjustment of feed gas oxygen concentration, feed gas alkylene concentration, reactor feed gas inlet pressure, and/or feed gas carbon dioxide concentration.

Example 1

A single pass continuous stirred tank reactor (CSTR) is loaded with 50 ml of whole pills of a high efficiency ethylene oxide catalyst. The catalyst is operated for 41 days and is lined out at an initial reactor outlet ethylene oxide concentration of 2.0%. The initial reaction temperature prior to the rate reduction is controlled to about 240° C. to maintain the target ethylene oxide production rate. The initial reactor inlet pressure is 2000 kPa, and the initial gas hourly space velocity is 6900 h$^{-1}$. The initial reactor feed gas molar composition is 30.0% ethylene, 8.0% oxygen, 1.0% carbon dioxide, 0.6% ethane, and the balance is nitrogen. The feed gas also includes an ethyl chloride gas phase promoter with a molar concentration that is controlled to maintain an optimum Z* value of 3.5.

On day 41, the target reactor outlet ethylene oxide molar concentration is reduced from 2.0% to 1.2%. To achieve the reduction in ethylene oxide molar concentration, the molar concentration of oxygen in the feed gas is reduced from 8.0% to 4.0%, the molar concentration of ethylene in the feed gas is reduced from 30.0% to 25.0%, and the pressure is reduced from 2000 kPa to 1890 kPa. To simulate the effects of using a constant speed recycle gas compressor, the gas hourly space velocity is reduced in proportion to the reduction of the reactor pressure, i.e., from 6900 h$^{-1}$ to 6300 h$^{-1}$. The concentration of ethyl chloride in the reactor feed gas is reduced from 3.15 ppm to 2.98 ppm to maintain Z* at 3.5. The foregoing changes are made almost simultaneously.

Figure 4A:
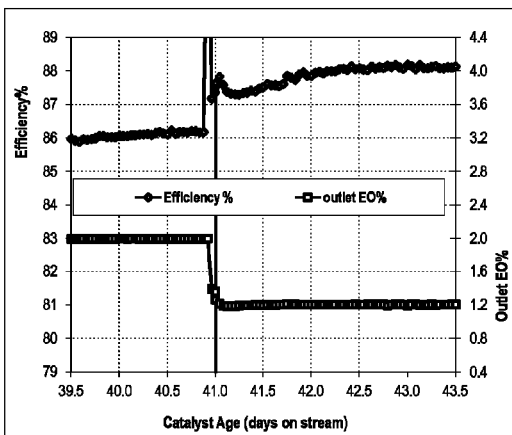
FIG. 4A is a graph depicting efficiency and reactor product ethylene oxide concentration data used to illustrate an exemplary a method of reducing ethylene oxide concentration by reducing feed gas oxygen concentration, feed gas alkylene concentration, and reactor inlet pressure in a process for producing ethylene oxide using a high-efficiency catalyst.
Figure 4B:
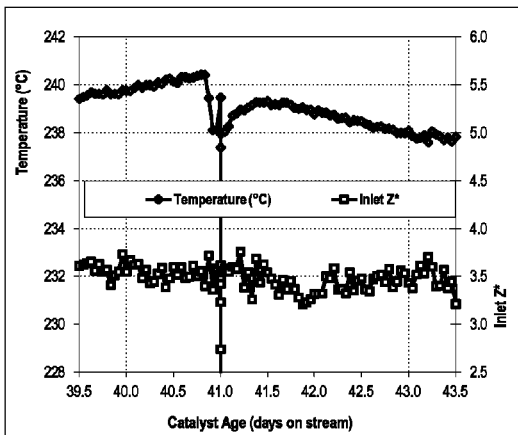
FIG. 4B is a graph depicting reaction temperature and overall chloriding effectiveness data used to illustrate the exemplary method of FIG. 4A.

The results of the foregoing process changes are depicted in FIGS. 4A-4B. As the figures indicate, the efficiency increases from about 86% to about 88% whereas the reaction temperature decreases by about 2° C. Thus, the method of Example 1 effectively decreases the concentration of ethylene oxide in the reaction product without requiring the manipulation of reaction temperature and/or overall chloriding effectiveness.

Example 2

Comparative

The comparative example is carried out using the same process as in Example 1 following the process changes that are described therein. On day 44, the catalyst is briefly shut down. Following re-start at the same conditions used prior to shut-down, steady-state operation is re-established after 3 days. The same 88% efficiency is obtained, but the reaction temperature is 2° C. higher than before. On day 48, the reactor outlet ethylene oxide concentration is 1.2%, but the process conditions are reversed relative to the changes made in Example 1 to restore the initial concentrations of feed gas oxygen and ethylene, the initial reactor pressure, and the initial gas hourly space velocity used therein.

Figure 5A:
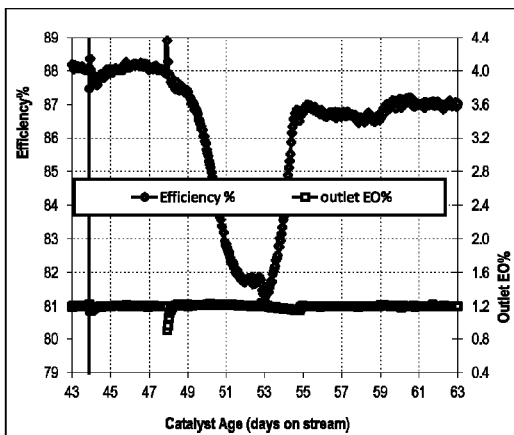
FIG. 5A is a graph depicting efficiency and reactor product ethylene oxide concentration data used to illustrate a conventional method of reducing ethylene oxide concentration by reducing reaction temperature in a process for producing ethylene oxide using a high-efficiency catalyst.
Figure 5B:
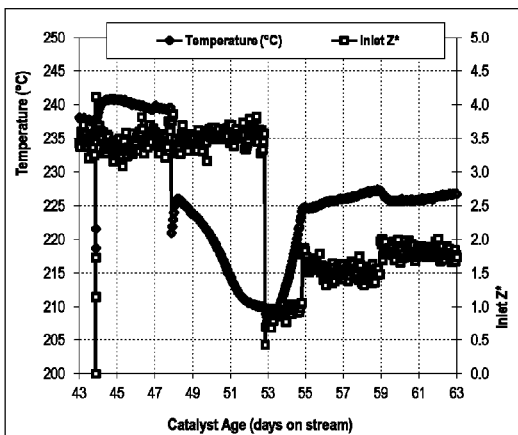
FIG. 5B is a graph depicting reaction temperature and overall chloriding effectiveness used to illustrate the conventional method of FIG. 5A.

To demonstrate the effects of using conventional techniques for reducing the reactor outlet ethylene oxide concentration, the reaction temperature is manually reduced to 225° C. based on a kinetic estimation of the temperature required to achieve an ethylene oxide concentration of 1.2%. The reactor is then placed on automatic temperature control to maintain the selected ethylene oxide concentration. The ethyl chloride and $Z^*$ values are not optimized prior to making these changes but are later adjusted (around day 53) to maximize efficiency. As shown in FIGS. 5A and 5B, the reaction temperature and efficiency experience strong variations that are difficult to manage. In addition, the process takes a relatively longer time (compared to Example 1) to re-optimize, and even after optimization, the process efficiency is about 1% lower than in Example 1.

Example 3

A feed gas comprising 35.0 mole % ethylene, 0.6% mole ethane, 8.0 mole % oxygen, 2.0 mole % CO2 and 1.9-2.1 ppmv ethyl chloride, and the balance nitrogen is introduced to a high efficiency, rhenium-promoted silver catalyst loaded in a pilot plant reactor with reactor volume of 3.55 liters. The reactor pressure is 2135 kPa, and the total feed gas flow rate is 19169 standard liters per hr. The inlet coolant temperature is 230° C. throughout the run. Inlet coolant temperature (upper trend) and $Z^*$ (lower trend) profiles are given in FIG. 6A.

Figure 6C:
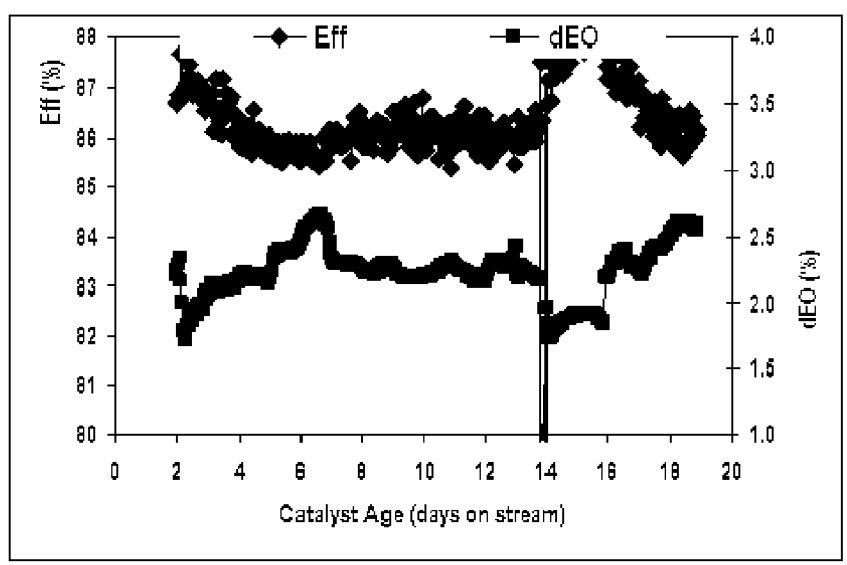
FIG. 6C is a graph depicting efficiency and reactor product delta ethylene oxide concentration data used to illustrate the exemplary method of FIG. 6A.

As shown in FIG. 6C, by day 6.5, the delta ethylene oxide molar concentration (lower trend) is increased to 2.66%, and catalyst efficiency (upper trend) has attained a stable value of 85.7%. On day 7, the molar concentration of oxygen in the feed gas is reduced from 8.0% to 5.7% without changing any other process variables. The trends for oxygen (upper trend) and ethylene molar concentration (lower trend) are given in FIG. 6B. On day 7, the delta ethylene oxide molar concentration is reduced to 2.2% as a result of the drop in oxygen molar concentration in the feed gas composition. During the same time, the catalyst selectivity increases to an average value of 86.0% from 85.7%. The reduction in oxygen molar concentration results in a decrease in the delta ethylene oxide molar concentration without requiring the manipulation of other process variables to maintain optimum efficiency. From day 16 onward, the molar concentration of oxygen in the feed gas is increased to 8.5%. By day 18, the delta ethylene oxide molar concentration increases to 2.6%, and catalyst efficiency reaches 86.0%. Thus, this example illustrates the use of feed gas oxygen concentration to effect a desired change in alkylene oxide concentration without compromising efficiency.

Example 4

Figure 7A:
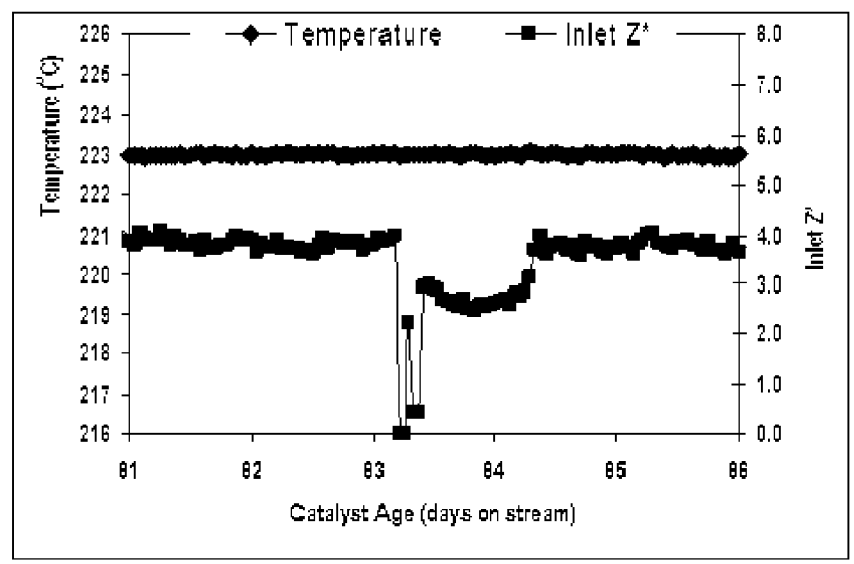
FIG. 7A is a graph depicting reaction temperature and overall catalyst chloriding effectiveness used to illustrate the effects of decreasing oxygen concentration on reactor product ethylene oxide concentration when operating at a non-optimal and optimal overall catalyst chloriding effectiveness.

A feed gas comprising 35.0 mole % ethylene, 0.6 mole % ethane, 8.5 mole % oxygen, 1.0 mole % CO2 and 3.2 ppmv ethyl chloride, and the balance nitrogen is introduced to a high efficiency, rhenium-promoted silver catalyst loaded in a pilot plant reactor with reactor volume of 3.20 liters. The reactor pressure is 2135 kPa, and the total feed gas flow rate is 17245 standard liters per hr. The inlet coolant temperature is 223° C. throughout the run. Inlet coolant temperature (upper trend) and $Z^*$ (lower trend) profiles are given in FIG. 7A.

Figure 7B:
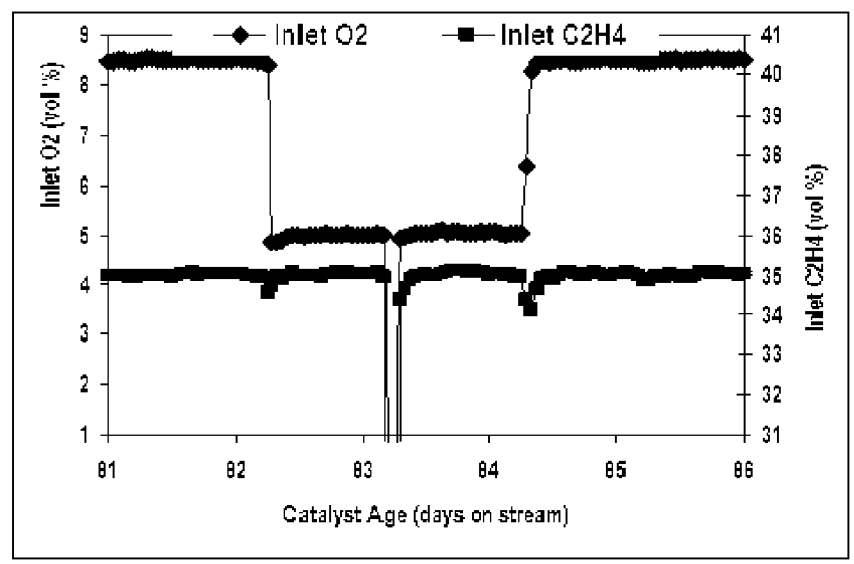
FIG. 7B is a graph depicting feed gas oxygen and feed gas ethylene concentration used to illustrate the exemplary method of FIG. 7A.
Figure 7C:
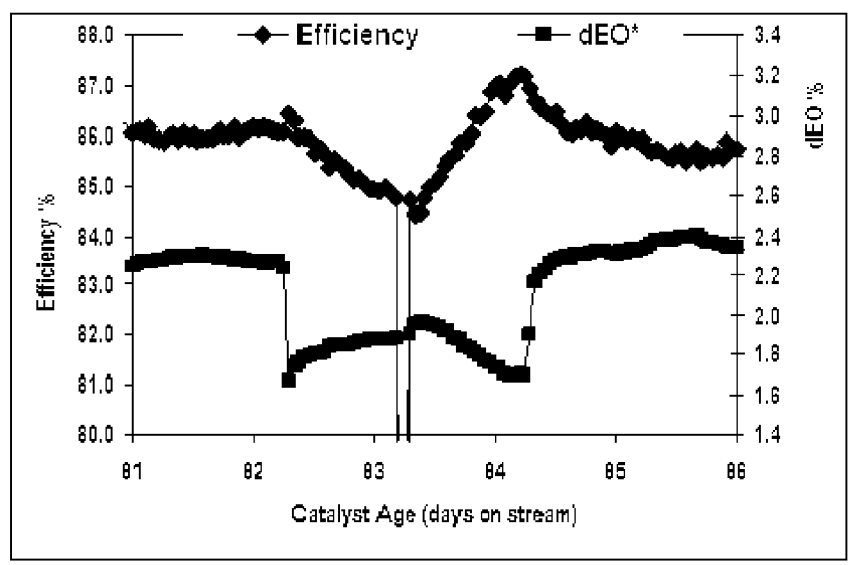
FIG. 7C is a graph depicting efficiency and reactor product delta ethylene oxide concentration data used to illustrate the exemplary method of FIG. 7A.

As shown in FIG. 7C, between days 82 to 82.5, the target delta ethylene oxide molar concentration (lower trend) decreases from 2.3% to 1.7%, and by day 83, the target delta ethylene oxide molar concentration increases to 1.9%. The catalyst efficiency (upper trend) during this time period decreases by 1.0%. To realize the reduction in ethylene oxide molar concentration, the molar concentration of oxygen in the feed gas is reduced from 8.5% to 5.0% without changing any other process variables. The trends for oxygen (upper trend) and ethylene (lower trend) molar concentration are given in FIG. 7B. The changes in delta ethylene oxide molar concentration and catalyst efficiency at lower oxygen molar concentration suggest that the chloride effectiveness factor is on the higher side of its optimum value. Thus, the catalyst is showing over-chloriding behavior.

Between days 83 to 83.5, the reaction is shut down for 2 hours, and started-up again at pre-shutdown conditions except the ethyl chloride is set at 2.1 ppmv, resulting in an average $Z^*$ value of 2.7, which is lower compared to pre-trip conditions. As shown in FIG. 7C, after restart, by day 84, the target delta ethylene oxide molar concentration is reached at 1.7% and catalyst efficiency increases to 87.2%. Between days 84 to 85, the molar concentration of oxygen in the feed gas is again increased back to 8.5%. By day 86, the delta ethylene oxide molar concentration increases to 2.3%, and catalyst efficiency reaches 86.0%. Thus, when $Z^*$ is initially at an optimum value, feed gas oxygen can be adjusted to attain a desired delta ethylene oxide concentration without requiring the adjustment of other process variables to maintain a substantially optimum efficiency.

The methods described herein can also be used to maintain an alkylene oxide production parameter at a desired value when other process constraints would otherwise result in a higher than desired value. In one scenario, the process is limited by a minimum reaction temperature constraint, which can occur when the reactor coolant system 28 reaches a capacity constraint. For example, in those reactors that are cooled by a boiling water medium, the water flow is typically countercurrent to the flow of reactants, in which case the coolant side outlet 29 (FIG. 1) temperature is located proximate the reactor inlet 22 that receives the feed gas. In this case, the temperature of the coolant at the coolant inlet 31 inlet 22 will be controlled by a steam drum pressure controller (not shown, but downstream of the coolant outlet 29 temperature) that regulates the pressure of steam generated when the coolant absorbs the heat of reaction. To lower the coolant temperature at the coolant inlet 31, the steam drum pressure is reduced, which typically involves opening a control valve operatively connected to the steam drum. At some point the valve will open fully or otherwise be unable to further lower the steam drum pressure, at which point the cooling medium will be at its minimum achievable temperature at coolant inlet 31. As used herein, the phrase "minimum achievable (or attainable) reaction temperature" refers to the lowest reaction temperature that can be reached during epoxidation or the lowest reaction temperature at which stable operation of the epoxidation process can be maintained. The phrase "minimum achievable (or attainable) reactor coolant temperature" refers to the lowest coolant temperature that can be reached during epoxidation or the lowest reactor coolant temperature at which stable operation of the epoxidation process can be maintained.

In other scenarios, a non-aqueous coolant such as a hydrocarbon fluid may be used. One well known example of a hydrocarbon coolant fluid is tetralin (1,2,3,4-Tetrahydronaphthalene). In the case of hydrocarbon coolants, it may be preferable to orient the coolant flow co-currently with the reactor-side flow, in which case the coolant side inlet 31 would be proximate the reactor side inlet 22 (i.e., it would be opposite the orientation shown in FIG. 1). In one example, the hydrocarbon coolant absorbs the heat of reaction, and the heated hydrocarbon is then used to generate steam by exchanging its heat with boiling water in a heat exchanger (not shown). Because the coolant is recycled to the reactor 10, the extent to which the hot hydrocarbon can transfer heat to the boiling water will dictate the minimum achievable temperature at the coolant inlet, which in turn, will affect the minimum achievable reaction temperature. Thus, if the water side outlet of the coolant heat exchanger is connected to a steam drum with a pressure controller, once the pressure control valve is fully open or otherwise out of control, the water side of the coolant heat exchanger will be at its coolest possible temperature, and the hydrocarbon coolant exiting the heat exchanger and flowing into the coolant side of the reactor will be at its lowest possible value.

In certain situations, especially in the early life of a high efficiency silver catalyst when the catalyst activity is at its highest, the value of the alkylene oxide production parameter resulting from operation at a minimum reaction temperature may be higher than that which is desired when operating at the desired or target values of feed gas oxygen, alkylene, and carbon dioxide concentration (and/or partial pressure). Put differently, at the desired alkylene oxide production parameter, the target values of oxygen, alkylene, and carbon dioxide concentration (and/or partial pressure) may correspond to a reaction temperature lower than the minimum that is achievable. Thus, in accordance with one method, one or both of the feed gas oxygen and alkylene concentrations (and/or partial pressures) are maintained below their target values for a selected period of time so that operation at the minimum achievable reaction temperature yields the desired value of the alkylene oxide production parameter. In one variant of the method, the feed gas carbon dioxide concentration (and/or partial pressure) is increased above its target value while the feed gas oxygen and alkylene concentrations are held at their target values to yield the desired value of the alkylene oxide production parameter at the minimum achievable reaction temperature. However, it is generally preferable to adjust feed gas oxygen and/or alkylene concentrations below their target values before adjusting the feed gas carbon dioxide concentration above its target value because the feed gas carbon dioxide concentration may be hard to control on a short term basis and because it tends to be strongly affected by the alkylene oxide production parameter and the efficiency (selectivity) of the process toward the alkylene oxide.

Figure 8A:
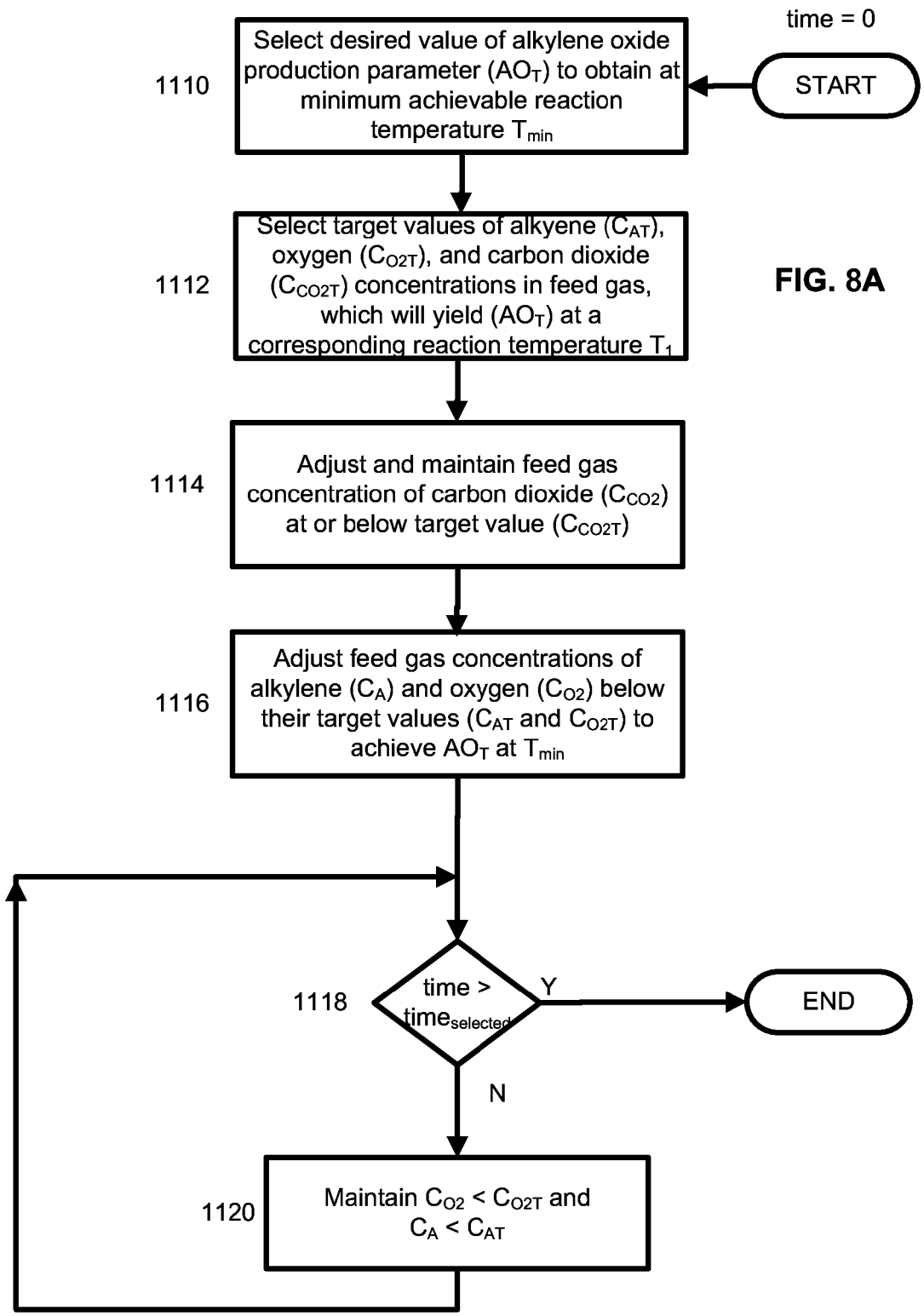
FIG. 8A is a flow chart depicting a method of maintaining a value of an alkylene oxide production parameter during the early life of a high efficiency catalyst by maintaining feed gas oxygen and alkylene concentrations below target values.

Referring to FIG. 8A, a method of maintaining a desired value of an alkylene oxide production parameter is described. In certain preferred embodiments, the method is carried out at start-up (i.e., when a reactive mixture of alkylene and oxygen are first supplied to reactor 10 at a reaction temperature sufficient to yield epoxidation) or after the completion of start-up (i.e., when alkylene oxide production is first detected). In accordance with the method, in step 1110 a desired or target value of an alkylene oxide production parameter ($AO_T$) is selected which is to be achieved while operating at a minimum reaction temperature $T_{min}$, or at least within a specified deviation (e.g., 1° C.) therefrom.

In step 1112, target values of feed gas concentrations (which correspond to respective partial pressures) of alkylene ($C_{AT}$), oxygen ($C_{O2}$) and carbon dioxide ($C_{CO2}$) are selected which would yield the target value of the alkylene oxide production parameter $AO_T$ at a corresponding reaction temperature $T_1$. In preferred embodiments, the corresponding reaction temperature $T_1$ will also correspond to an overall chloriding effectiveness value $Z^*_1$. In certain implementations, $T_1$ and $Z^*_1$ are individually or collectively optimized values or are within a specified deviation of such optimized values. The corresponding values of reaction temperature $T_1$ and overall chloriding effectiveness $Z^*_1$ may be determined using the methods described for determining initial conditions in step 202 in FIG. 2. These target values are those that are desired after the early life of the catalyst when the catalyst activity has dropped to a level where minimum reaction temperature operation is no longer required to keep the alkylene oxide production parameter at its desired level.

The target values ($C_{AT}$, $C_{O2T}$, $C_{CO2T}$) can be selected by a number of different methods. In one preferred method, the target value of oxygen concentration $C_{O2T}$ is selected based on flammability considerations, as noted above. The target concentration of oxygen $C_{O2T}$ in reactor feed stream 22 may vary over a wide range, and in practice, flammability is generally the limiting factor for oxygen concentration. Generally, the target oxygen concentration in reactor feed 22 will be at least one (1) mole percent, preferably at least two (2) mole percent, and still more preferably at least four (4) mole percent. The target oxygen concentration will generally be no more than fifteen (15) mole percent, preferably no more than twelve (12) mole percent, and even more preferably no more than nine (9) mole percent.

In certain exemplary processes, the target concentration of oxygen in reactor feed 22 is no greater than an amount of oxygen that would form a flammable mixture with the components of reactor feed 22 at the prevailing process conditions (the "oxygen flammability concentration"). In other embodiments, the target oxygen concentration is no greater than a pre-defined percentage of the oxygen flammability concentration (e.g., the maximum oxygen concentration is no greater than 95% of the oxygen flammability concentration and preferably no greater than 90% of the oxygen flammability concentration). In certain further embodiments, the target oxygen concentration and/or the oxygen flammability concentration is determined based on at least one variable selected from the group consisting of reaction temperature, pressure, alkylene concentration, alkylene oxide concentration, ballast gas concentration, and carbon dioxide concentration in reactor feed 22.

The target concentration of alkylene in reactor feed 22 is generally based on reaction system design limitations, catalyst performance, and an optimum trade-off with the maximum oxygen concentration allowed by safety considerations. The target concentration of alkylene in reactor feed stream 22 may vary over a wide range. However, it is preferably at least eighteen (18) mole percent and more preferably at least twenty (20) mole percent. The target concentration of alkylene in reactor feed stream 22 is preferably no greater than 50 mole percent, and more preferably is no greater than 40 mole percent.

The target carbon dioxide concentration is based on the carbon dioxide removal system design capacity and operational cost, catalyst efficiency, and reactor temperature limitations. Generally, lower carbon dioxide concentrations correspond to higher catalyst efficiency and activity. The target carbon dioxide concentration in reactor feed 22 is generally no more than 5 mole percent, preferably no more than 3 mole percent, and even more preferably no more than 2 mole percent of the total composition of reactor feed 22.

The corresponding values of reaction temperature $T_1$ and overall chloriding effectiveness $Z^*_1$ (i.e., the values corresponding to the target values of feed gas alkylene, oxygen, and carbon dioxide concentration) may be determined in a variety of ways, including those described with respect to step 202 of FIG. 2. In one example, a value of $Z^*_1$ is selected and $T_1$ is selected to achieve a maximum efficiency (selectivity) toward the alkylene oxide at the selected value of $Z^*_1$, the target alkylene oxide production parameter $AO_T$, and the target feed gas concentrations of alkylene, oxygen, and carbon dioxide. The selected value of $Z^*_1$ is preferably no less than 1.0. It is also preferably no greater than 20 and more preferably no greater than 15. In accordance with the method, the corresponding value of reaction temperature $T_1$ will be lower than the minimum achievable reaction temperature $T_{min}$. Thus, $T_1$ represents a desired, but unachievable reaction temperature.

In accordance with another technique, a value of $Z^*_1$ is selected, and $T_1$ is then selected to provide a first derivative of efficiency toward the alkylene oxide versus alkylene oxide production parameter at constant temperature, constant reactor inlet alkylene concentration, and a fixed process condition $(\partial E/\partial AO)_T$ within a specified range. The fixed process condition is one in which at least one variable selected from the group consisting of pressure, reactor inlet oxygen concentration, reactor inlet carbon dioxide concentration, and gas hourly space velocity is held at a constant value. In one preferred embodiment, the fixed process condition is a condition at which each of pressure, reactor inlet oxygen concentration, reactor inlet carbon dioxide concentration and gas hourly space velocity is held constant. In certain cases where the alkylene oxide production parameter AO is the reactor outlet alkylene oxide concentration, $(\partial E/\partial C_{AO})_T$ is preferably less than 0 percent efficiency/mole percent alkylene oxide, more preferably no greater than −1.5 percent efficiency/mole percent alkylene oxide, and even more preferably no greater than −2 percent efficiency/mole percent alkylene oxide. $(\partial E/\partial C_{AO})_T$ is preferably at least −5 percent efficiency/mole percent alkylene oxide, more preferably at least −4 percent efficiency/mole percent alkylene oxide, and even more preferably at least −4 percent efficiency/mole percent alkylene oxide. $(\partial E/\partial C_{AO})_T$ values of −3 percent efficiency/mole percent alkylene oxide are especially preferred.

In accordance with another technique, the corresponding reaction temperature $T_1$ and corresponding overall chloriding effectiveness value $Z^*_1$ are selected such that $Z^*_1$ is a specified fraction or multiple of the efficiency-maximizing value of $Z^*$ for the temperature $T_1$. In certain examples, $Z^*_1$ is set at a value that is preferably at least one percent greater than $Z^*_{max}$, (i.e., at least $1.01\ Z^*_{max}$) more preferably at least 5 percent greater than $Z^*_{max}$, and more preferably at least 10 percent greater than $Z^*_{max}$. $Z_1^*$ is preferably not more than 25 percent greater than $Z^*_{max}$ (i.e., not more than $1.25\ Z^*_{max}$), more preferably not more than 20 percent greater than $Z^*_{max}$, and even more preferably not more than 15 percent greater than $Z^*_{max}$. $AO_T$ and the value of $Z_1^*$ will determine $T_1$ and a corresponding efficiency.

In accordance with yet another technique, the overall chloriding effectiveness $Z^*_1$ and reaction temperature $T_1$ corresponding to the target values ($C_{AT}$, $C_{O2T}$, $C_{CO2T}$) are an optimized combination of $Z^*$ and T determined by determining efficiency (selectivity) towards alkylene oxide at a variety of values of the alkylene oxide production parameter AO as $Z^*$ is varied over a specified range at a plurality of reaction temperatures. In certain examples, the optimization is carried out while holding the feed gas concentration of alkylene constant at a fixed process condition. In one example, the fixed process condition is one at which one or more process variables selected from the group consisting of feed gas pressure, feed gas oxygen concentration, feed gas carbon dioxide concentration and gas hourly space velocity is held constant. In another example, each of these variables is held constant during the optimization process.

Referring again to FIG. 8A, in step 1114 the feed gas concentration of carbon dioxide $C_{CO2}$ (and/or its partial pressure $p_{CO2}$) is adjusted to a value that is at or below its target value $C_{CO2T}$. In certain embodiments, $Z^*$ remains substantially constant at the previously selected corresponding value $Z^*_1$ during this step. In other embodiments, $Z^*$ remains substantially constant at a value corresponding to the minimum achievable reaction temperature, $T_{min}$ (such as an optimum value of $Z^*$ corresponding to $T_{min}$, at the target feed concentration values of ethylene, oxygen, and carbon dioxide). In step 1116, the feed gas concentrations of alkylene $C_A$ and oxygen $C_{O2}$ are adjusted below their respective target values $C_{AT}$ and $C_{O2T}$. In step 1118 the elapsed time since the commencement of the method is checked to see if it exceeds a selected time $t_{selected}$. If the elapsed time has exceeded $t_{selected}$, the method ends.

In certain examples, the selected time $t_{selected}$ is one at which the high efficiency catalyst activity has declined sufficiently such that the target value of the alkylene oxide production parameter $AO_T$ can be achieved at the target feed gas concentrations of alkylene, oxygen, and carbon dioxide ($C_{AT}$, $C_{O2T}$ and $C_{CO2T}$, respectively) while operating at the minimum reaction temperature $T_{min}$. In certain implementations, the selected time $t_{selected}$ is no more than one year, preferably no more than eight (8) months, and even more preferably, no more than four (6) months. In certain implementations, $t_{selected}$ is no less than one (1) month, preferably no less than 2 months, and more preferably, no less than four (4) months. In specific examples provided below, $t_{selected}$ is five (5) months.

If in step 1118 the elapsed time has not exceeded the selected time $t_{selected}$, the method proceeds to step 1120 wherein the feed gas concentrations of oxygen $C_{O2}$ and alkylene $C_A$ are maintained below their target values $C_{AT}$ and $C_{O2T}$. In certain preferred embodiments, $Z^*$ remains substantially constant at the selected corresponding value $Z^*_1$ during this step by modifying the amount of organic chloride gas phase promoter 14. In other preferred embodiments, $Z^*$ remains substantially constant at a value corresponding to the minimum achievable reaction temperature, $T_{min}$, (such as an optimum value of $Z^*$ corresponding to $T_{min}$, at the target feed concentration values of ethylene, oxygen, and carbon dioxide). The values of feed gas oxygen and alkylene concentration $C_{O2}$ and $C_A$ are selected to achieve the desired value of the alkylene oxide production parameter $AO_T$ (or to stay within a specified deviation thereof, such as 5%) at the minimum reaction temperature $T_{min}$, (or at a specified deviation therefrom, such as 1° C.). In one example, the alkylene oxide production parameter is the alkylene oxide work rate.

Step 1120 may be carried out in a number of ways. In one implementation, the feed gas concentrations of oxygen $C_{O2}$ and alkylene $C_A$ are held at a substantially constant value below their target values $C_{O2T}$ and $C_{AT}$ for all or a part of the selected time $t_{selected}$. Either or both of the values of each feed gas concentration may be increased to the target value in a single step at the end of the selected time period $t_{selected}$. Alternatively, either or both of the values may be increased to their target values by a series of step changes, step changes combined with ramp changes, non-linear and variable rate, or combinations thereof, during the selected time period $t_{selected}$. In certain examples, described below, the feed gas alkylene concentration $C_A$ is increased towards its target value $C_{AT}$ in accordance with multiple substantially linear functions of varying slope over the selected time period $t_{selected}$ while the oxygen concentration $C_{O2}$ is held at a substantially constant value for an initial period of time less than the selected period of time $t_{selected}$, after which it is also linearly increased to its target value $C_{O2T}$ such that it reaches the target value at the end of the selected time period $t_{selected}$. After step 1120, control returns to step 1118 to again determine whether the elapsed time has exceeded the selected time $t_{selected}$.

In FIG. 8A, both the feed gas oxygen $C_{O2}$ and feed gas alkylene $C_A$ concentrations are maintained below their target values $C_{O2T}$ and $C_{AT}$ during the selected time period $t_{selected}$. However, in one variation, the feed gas alkylene concentration $C_A$ may be held at its target value $C_{AT}$ throughout the selected time period $t_{selected}$ while only the feed gas oxygen concentration $C_{O2}$ is maintained below its target value in step 1120. Conversely, the feed gas oxygen concentration $C_{O2}$ may be held at its target value $C_{O2T}$ throughout the selected time period $t_{selected}$ while only the feed gas alkylene concentration $C_A$ is held below its target value $C_{AT}$. In either variation, step 1120 is preferably carried out at a substantially constant $Z^*$ value such that the alkylene oxide production parameter AO is substantially equal (or within a specified deviation, such as 5%) of its target value $AO_T$.

Figure 8B:
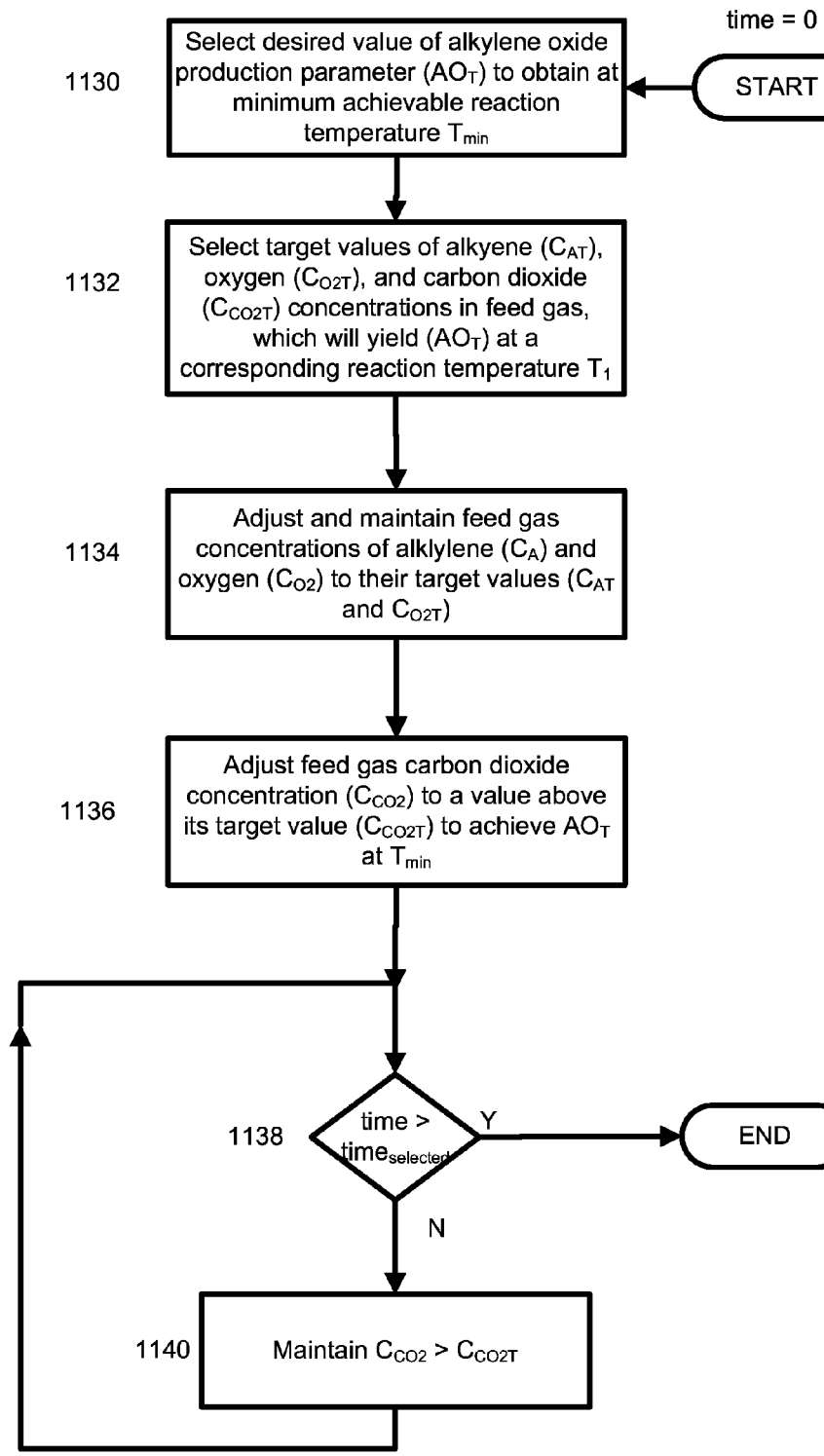
FIG. 8B is a flow chart depicting a method of maintaining a value of an alkylene oxide production parameter during the early life of a high efficiency catalyst by maintaining feed gas carbon dioxide concentration above a target value.

Another exemplary method of maintaining a selected alkylene oxide production parameter value $AO_T$ while operating at a minimum reaction temperature $T_{min}$, is depicted in FIG. 8B. In accordance with the method, steps 1130 and 1132 are carried out similarly to steps 1110 and 1112 of FIG. 8A. In step 1134 the feed gas concentrations of alkylene $C_A$ and oxygen $C_{O2}$ are adjusted to their respective target values $C_{AT}$ and $C_{O2T}$, preferably while maintaining a substantially constant $Z^*$ value, that is more preferably a value that corresponds to the feed gas concentration target values ($C_{AT}$, $C_{O2T}$, $C_{CO2T}$) and the minimum achievable reaction temperature $T_{min}$, (such as an optimum value of $Z^*$ corresponding to $T_{min}$, at the target feed concentration values of ethylene, oxygen, and carbon dioxide). However, in certain embodiments, $Z^*$ is maintained at a substantially constant value of $Z^*_1$ which corresponds to the reaction temperature $T_1$.

In step 1136, the feed gas concentration of carbon dioxide $C_{CO2}$ (and/or its partial pressure) is adjusted to a value above its target value $C_{CO2T}$ to achieve the selected value of the alkylene oxide production parameter $AO_T$ while operating at the minimum reaction temperature of $T_{min}$. $Z^*$ preferably remains substantially constant during this step and is more preferably substantially equal to $Z^*_1$. The feed gas concentration of carbon dioxide $C_{CO2}$ may be increased by the methods described previously (linear functions, step functions, non-linear functions, or combinations thereof).

In step 1138, the elapsed time since the beginning of the method is compared to the selected time $t_{selected}$. If the elapsed time has exceeded $t_{selected}$, the method ends. Otherwise, the method proceeds to step 1140 wherein the feed gas concentration of carbon dioxide $C_{CO2}$ is maintained above its target value $C_{CO2T}$ such that the target value of the alkylene oxide production parameter (or a specified deviation therefrom, such as 5%) is achieved while the reaction temperature remains at the minimum reaction temperature $T_{min}$ (or within a specified deviation therefrom, such as 1° C.). In certain preferred embodiments, $Z^*$ remains substantially constant at the selected corresponding value $Z^*_1$ during this step. Following step 1140, control returns to step 1138 where the elapsed time is again compared to the selected time $t_{selected}$.

In step 1140, the feed gas carbon dioxide concentration $C_{CO2}$ may be held at a substantially constant value above its target value, or it may be held at a variety of values above the target value. The concentration $C_{CO2}$ may be decreased to the target value in a single step at the end of the selected time period $t_{selected}$. Alternatively, the value may be decreased to the target value by a series of step changes, step changes combined with ramp changes, or non-linear and variable rate changes during the selected time period $t_{selected}$. In certain examples, as described below, the feed gas carbon dioxide concentration $C_{CO2}$ is decreased towards its target value $C_{CO2T}$ in accordance with multiple substantially linear functions of varying slope over the selected time period $t_{selected}$.

In FIG. 8B, feed gas concentrations of oxygen $C_{O2}$ and alkylene $C_A$ are held at (or within a specified deviation from) their target values $C_{O2}$ and $C_A$ while the feed gas concentration of carbon dioxide $C_{CO2}$ is maintained above its target value $C_{CO2T}$ during the selected period of time $t_{selected}$. However, in additional exemplary methods, the feed gas concentration of oxygen $C_{O2}$ may be adjusted and maintained below its target value $C_{O2T}$ during the selected time period $t_{selected}$ in accordance with the method of FIG. 8A while the feed gas carbon dioxide concentration $C_{CO2}$ may be adjusted and maintained above its target value $C_{CO2T}$ during the selected time period $t_{selected}$ in accordance with the method of FIG. 8B to maintain the alkylene oxide production parameter at its target value $AO_T$ while operating at the minimum reaction temperature $T_{min}$ and the target feed gas alkylene concentration $C_{AT}$. In addition, the feed gas concentration of alkylene $C_A$ may be adjusted and maintained below its target value $C_{AT}$ during the selected time period $t_{selected}$ in accordance with the method of FIG. 8A while the feed gas carbon dioxide concentration $C_{CO2}$ may be adjusted and maintained above its target value $C_{CO2T}$ during the selected time period $t_{selected}$ in accordance with the method of FIG. 8B to maintain the alkylene oxide production parameter AO at its target value $AO_T$ while operating at the minimum reaction temperature $T_{min}$ and the target feed gas oxygen concentration $C_{O2T}$. Alternatively, the methods of FIGS. 8A and 8B may be combined such that the feed gas concentrations of oxygen and alkylene $C_{O2}$ and $C_A$ are adjusted and maintained below their target values $C_{O2T}$ and $C_{AT}$ during the selected time period $t_{selected}$ and the feed gas carbon dioxide concentration $C_{CO2}$ is held above its target value $C_{CO2T}$ during the selected time period $T_{selected}$ to maintain the alkylene oxide production parameter at its target value $AO_T$ while operating at the minimum reaction temperature $T_{min}$.

In certain cases, it may be desirable to make progressive changes in feed gas oxygen, alkylene and/or carbon dioxide concentrations ($C_{O2}$, $C_A$, $C_{CO2}$) away from their respective target values ($C_{O2T}$, $C_{AT}$, $C_{CO2T}$) to determine the required deviation from the target values that is necessary to achieve the target alkylene oxide production parameter $AO_T$ value while operating at the minimum reaction temperature $T_{min}$.

In accordance with one implementation of the method, a minimum feed gas oxygen concentration $C_{O2MIN}$ and a minimum feed gas alkylene concentration $C_{AMIN}$ are selected, and the feed gas oxygen concentration $C_{O2}$ and alkylene concentrations $C_A$ are kept above their respective minimum values $C_{O2MIN}$, $C_{AMIN}$ while being maintained below their target values $C_{O2T}$, $C_{AT}$.

In one example, the alkylene oxide production parameter AO is routinely monitored for comparison to the target value $AO_T$, such as by using on-line analyzers or sampling of product concentrations, and the feed gas oxygen and/or alkylene concentrations $C_{O2}$, $C_A$ are reduced as needed to maintain the alkylene oxide production parameter AO at its target value $AO_T$ (or within a selected deviation therefrom, such as 5%) while maintaining the reaction temperature T at the minimum value $T_{min}$ (or at a selected deviation therefrom, such as 1° C.). As noted previously, the "reaction temperature" may be measured in a number of ways, including by using the coolant inlet or outlet temperature. However, in a preferred embodiment, the coolant inlet temperature 31 is used as an indicator of reaction temperature.

In another example, once the minimum values of the oxygen $C_{O2MIN}$ and alkylene $C_{AMIN}$ concentrations in the feed gas are reached, a target value of carbon dioxide concentration $C_{CO2T}$ in the feed gas is selected, and the feed gas carbon dioxide concentration $C_{CO2}$ is increased as necessary to maintain the alkylene oxide production AO parameter at the desired value $AO_T$ and the reaction temperature T at the minimum value $T_{min}$.

Figure 8C:
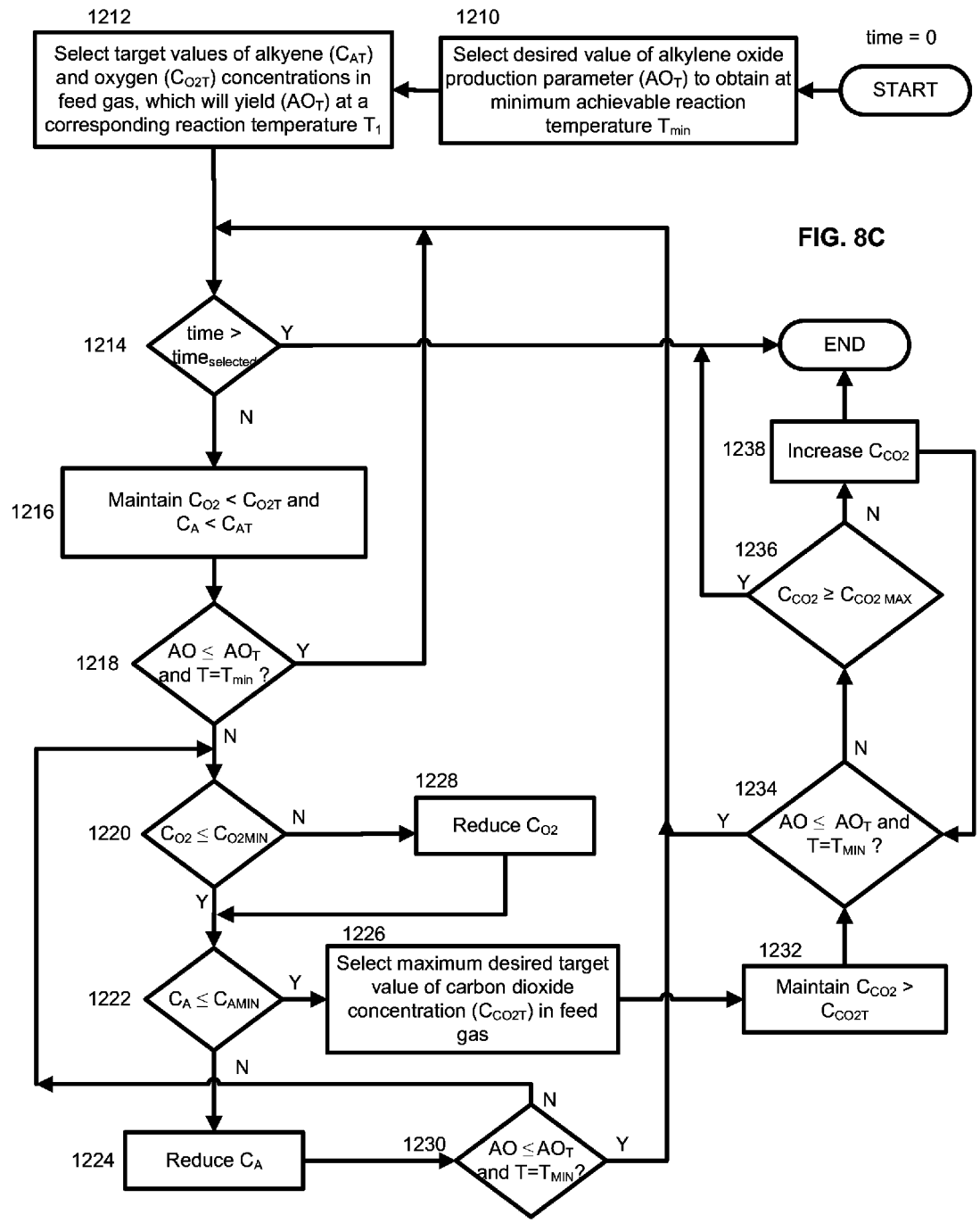
FIG. 8C is a flow chart depicting a method of maintaining a value of an alkylene oxide production parameter during the early life of a high efficiency catalyst by maintaining feed gas alkylene and oxygen concentrations below target values and feed gas carbon dioxide concentration above a target value.

Referring to FIG. 8C, a method of maintaining a desired or target value of an alkylene oxide production parameter $AO_T$ at a minimum reaction temperature $T_{min}$, such as one dictated by the aforementioned cooling circuit limitations, will be described. In accordance with the method, a desired value $AO_T$ of the alkylene oxide production parameter is selected (Step 1210). The process 20 is operated at $T_{min}$ to achieve the desired alkylene oxide production parameter value $AO_T$.

In step 1212, target values of alkylene feed gas concentration $C_{AT}$ and oxygen feed gas concentration $C_{O2}$ are selected based on the considerations described above with respect to step 1112 of FIG. 8A. In addition, minimum values of the feed gas oxygen and alkylene concentrations $C_{O2MIN}$ and $C_{AMIN}$ may be selected in step 1212. $C_{O2MIN}$ is a selected lower limit of the feed gas oxygen concentration. $C_{O2MIN}$ may be determined based on a number of considerations, for example, such as ensuring that there is some amount of oxygen breakthrough and/or the prevention of soot generation. In certain examples, $C_{O2MIN}$ is preferably no less than one (1) mole percent, more preferably no less than two (2) mole percent, and even more preferably no less than four (4) mole percent. In additional examples, $C_{O2MIN}$ corresponds to a minimum feed gas oxygen partial pressure $p_{min}$ that is preferably no less than 7 kPa, more preferably no less than 14 kPa, and still more preferably no less than 30 kPa.

Similarly, a minimum feed gas alkylene concentration $C_{AMIN}$ may be set based on considerations including the acceptable range of catalyst efficiency and stability and process operability (e.g., process control capability, the impact of reducing alkylene concentration on recycle flow rate, and reaction pressure control). In certain examples, $C_{AMIN}$ is preferably no less than fifteen (15) mole percent, more preferably no less than eighteen (18) mole percent, and even more preferably no less than twenty (20) mole percent. $C_{AMIN}$ preferably corresponds to a minimum feed gas alkylene partial pressure that is at preferably at least 97 kPa psia, more preferably at least 117 kPa, and even more preferably at least 131 kPa.

In step 1212 corresponding values of the overall chloriding effectiveness $Z^*_1$ and reaction temperature $T_1$ are also selected as described previously, with $T_1$ being less than the minimum reaction temperature $T_{min}$. In one preferred embodiment, the selected values of $Z^*_1$ and $T_1$ are an optimized combination of these two variables of the type described previously with respect to step 202.

In step 1214, it is determined whether the method of FIG. 8C has been in use for more than a selected period of time $t_{selected}$. If it has, the method ends. Otherwise, the method proceeds to step 1216 wherein the feed gas oxygen concentration $C_{O2}$ and feed gas alkylene concentration $C_A$ are set and maintained at values below their target values $C_{O2T}$ and $C_{AT}$. In certain preferred embodiments, $Z^*$ remains substantially constant at the selected corresponding value $Z^*_1$ during this step. The selected values of $C_{O2}$ and $C_A$ may be such that the alkylene oxide production parameter AO decreases but remains above its target value $AO_T$, requiring further process adjustments.

The feed gas oxygen and alkylene concentrations $C_{O2}$ and $C_A$ may be reduced by reducing the flow rates of their respective inlet streams 12 and 15 and/or by increasing the flow rate of ballast gas 13. In addition, the oxygen and alkylene concentrations $CO_2$ and $C_A$ need not both be reduced below their respective target values $C_{O2T}$ and $CA_T$. In certain examples, only one of them is reduced and the other is maintained at its target value. However, in FIG. 8C, both are reduced and maintained below their target values.

In step 1218, the alkylene oxide production parameter AO is compared to its target value $AO_T$. If AO remains below or equal to $AO_T$ (or at least no greater than a specified deviation amount above $AO_T$, such as 5%), and the reaction temperature remains substantially at $T_{min}$ (or no greater than a specified deviation amount above $T_{min}$, such as 1° C.), the method returns to step 1214. Otherwise, the method proceeds to step 1220. In certain examples, if AO is more than a specified deviation (e.g., 5%) below $AO_T$, the process is adjusted to increase AO toward $AO_T$ such as by increasing the feed gas oxygen and/or alkylene concentration or by increasing the reaction temperature. In certain examples, the decrease of AO by such an amount may indicate that the reaction temperature is no longer constraining, and the method may be terminated.

In step 1220, the feed gas oxygen concentration $C_{O2}$ is compared to minimum value $C_{O2MIN}$. In step 1220, if $C_{O2}$ is less than or equal to $C_{O2MIN}$, no further reductions in feed gas oxygen concentration are made, and control transfers to step 1222. If $C_{O2}$ is greater than (i.e., not less than or equal to) $C_{O2MIN}$, then in step 1228 the feed gas oxygen concentration $C_{O2}$ is reduced by a selected amount. In certain preferred embodiments, $Z^*$ remains substantially constant at the previously selected corresponding value $Z^*_1$ during this step.

In step 1222, the feed gas alkylene concentration $C_A$ is compared to the selected minimum feed gas alkylene concentration $C_{AMIN}$. If $C_A$ is less than or equal to $C_{AMIN}$, control transfers to step 1226. Otherwise, the feed gas alkylene concentration $C_A$ is reduced by a selected amount in step 1224, while $Z^*$ is preferably held at a substantially constant value, which is more preferably the selected value $Z^*_1$. In step 1230, the alkylene oxide production parameter AO is compared to the target value $AO_T$, and the reaction temperature T is compared to the minimum reaction temperature $T_{MIN}$. If the target value of the alkylene oxide production parameter $AO_T$ is exceeded (or if the target value is exceeded by more than a specified deviation such as 5%) or if the reaction temperature has risen above $T_{MIN}$ (or has exceeded it by more than a specified deviation such as 1° C.) control returns to step 1220. Otherwise, control returns to step 1214. In certain examples, in step 1230 if AO is more than a specified deviation (e.g., 5%) below $AO_T$, the process is adjusted to increase AO toward $AO_T$ such as by increasing the feed gas oxygen and/or alkylene concentration or by increasing the reaction temperature. In certain examples, the decrease of AO by such an amount may indicate that the reaction temperature is no longer constraining, and the method may be terminated.

If the comparison made in step 1222 indicates that the feed gas alkylene concentration $C_A$ is at or has fallen below the selected minimum, $C_{AMIN}$, the feed gas concentration of carbon dioxide $C_{CO2}$ is used to reduce the alkylene oxide production AO parameter to its target value $AO_T$. In step 1226, a maximum desired target value of feed gas carbon dioxide concentration $C_{CO2T}$ is selected as described previously for step 1112 in FIG. 8A ($C_{CO2T}$ may also be selected earlier such as in step 1212 if desired). In addition, a maximum value of the carbon dioxide concentration $C_{CO2MAX}$ may be selected, which is a value that will not be exceeded as concentration changes are made above the target value $C_{CO2T}$. In step 1232, the feed gas carbon dioxide concentration $C_{CO2}$ is set and maintained at a value above its target value of $C_{CO2T}$. $C_{CO2MAX}$ is preferably no greater than ten (10) mole percent, more preferably no greater than eight (8) mole percent, and even more preferably no greater than six (6) mole percent of the total feed gas composition.

Step 1234 is substantially the same as steps 1218 and 1230. If the alkylene oxide production parameter AO is less than or equal to the target value $A_{OT}$ (or if the target value is exceeded by no more than a specified deviation, such as 5%) and if the reaction temperature T is equal to the minimum temperature $T_{min}$ (or has exceeded it by no more than a specified deviation such as 1° C.), control transfers to step 1214. Otherwise, the method proceeds to step 1236 in which the feed gas carbon dioxide concentration $C_{CO2}$ is compared to the selected maximum feed gas carbon dioxide concentration $C_{CO2MAX}$. If the feed gas carbon dioxide concentration $C_{CO2}$ is equal to or exceeds the maximum value $C_{CO2MAX}$, the method ends. Otherwise, the feed gas carbon dioxide concentration $C_{CO2}$ is increased by a selected amount in step 1238, and control returns to step 1234. In certain preferred embodiments, $Z^*$ remains substantially constant at the selected corresponding value $Z^*_1$ during this step. In other preferred embodiments, $Z^*$ remains substantially constant at a value of $Z^*$ corresponding to the minimum reaction temperature, Tmin. In certain examples, in step 1234 if AO is more than a specified deviation (e.g., 5%) below $A_{OT}$, the process is adjusted to increase AO toward $A_{OT}$ such as by increasing the feed gas oxygen and/or alkylene concentration or by increasing the reaction temperature. In certain examples, the decrease of AO by such an amount may indicate that the reaction temperature is no longer constraining, and the method may be terminated.

In step 1228, the feed gas oxygen concentration $C_{O2}$ may be adjusted using the same techniques described for step 1120 of FIG. 8A. Thus, it may be adjusted using linear functions, step functions, non-linear functions, or various combinations of the three. The feed gas alkylene concentration $C_A$ may be adjusted similarly in step 1224, and the feed gas concentration of carbon dioxide $C_{CO2}$ may be increased using similar techniques in step 1238. Moreover, the progressive adjustments and comparisons of the alkylene oxide production parameter AO to its target value $AO_T$ may be made with oxygen alone, alkylene alone, carbon dioxide alone, oxygen and carbon dioxide, and alkylene and carbon dioxide.

Once the desired alkylene oxide production parameter $AO_T$ is achieved and a selected period of time has elapsed (such as $t_{selected}$, described previously), the process 20 can be adjusted to move the feed gas compositions $C_{O2}$, $C_A$, and $C_{CO2}$ toward their respective target values $C_{O2T}$, $C_{AT}$, and $C_{CO2T}$. In one preferred example, the carbon dioxide concentration $C_{CO2}$ is decreased to its target level $C_{CO2T}$ before increasing the feed gas concentrations of $C_{O2}$ and $C_A$ toward their respective target values $C_{O2T}$ and $C_{AT}$.

The methods of FIGS. 8A-8C will now be illustrated by way of the following examples.

Example 5

Figure 9A:
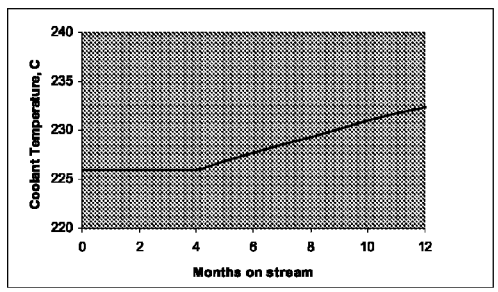
FIG. 9A is graph depicting reaction temperature as indicated by a reactor coolant inlet temperature used to illustrate the effect of operating at a minimum reaction temperature constraint while maintaining feed gas concentrations of oxygen, alkylene, and carbon dioxide at target values.
Figure 9B:
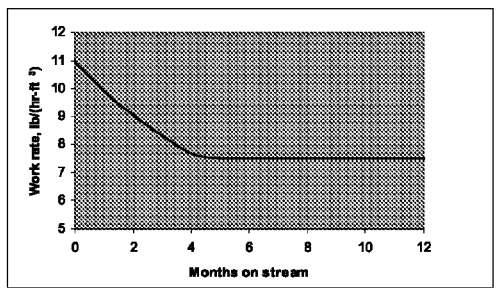
FIG. 9B is a graph depicting the alkylene oxide work rate corresponding to the conditions of FIG. 9A.

A simulation is carried out to predict the effects of reducing oxygen and ethylene feed gas concentrations to maintain a desired work rate at a constrained reaction temperature in a process for making ethylene oxide using a high efficiency catalyst. An ethylene oxide reactor is charged with a high-efficiency, rhenium promoted catalyst. Feed gas pressure is 282 psia (1944 KPa absolute), $Z^*$ is 2.7, and the reaction temperature (i.e., reactor coolant temperature) is 225° C. Ethylene oxide work rate is selected as the alkylene oxide production parameter to be monitored, and its target value $AO_T$ is set at 7.49 lb ethylene oxide/(hr-ft3 catalyst) (i.e., 120 kg ethylene oxide/hr-m³ catalyst). The target feed gas oxygen concentration $C_{O2T}$ is 7.6%, and the target feed gas ethylene concentration $C_{AT}$ is 31%. All concentrations stated herein are on a molar basis. The target feed gas carbon dioxide concentration $C_{CO2T}$ is 1.2%, and the gas hourly space velocity is 3100 hr⁻¹. At these conditions, the predicted corresponding starting coolant temperature $T_1$ is 216° C. However, the process has a minimum coolant temperature constraint $T_{MIN}$ of 226° C. Considering that 226° C. is the lower limit of coolant temperature, the reactor cannot be operated below 226° C. With a feed gas comprising 7.6% oxygen and 31% ethylene at a 226° C. coolant temperature, the work-rate during reactor start-up AO is estimated to be around 10.96 lb ethylene oxide/(hr-ft3 catalyst) (i.e., 176 kg ethylene oxide/hr-m³ catalyst) which is significantly higher than the target work-rate $AO_T$ of 7.49 lb/(hr-ft3 catalyst)(i.e., 120 kg ethylene oxide/hr-m³ catalyst). FIGS. 9A and 9B illustrate work rate and coolant temperature data wherein the coolant temperature is held at the lower limit of 226° C. for a period of four (4) months at the target values of feed gas oxygen and ethylene concentrations. The figure demonstrates that at these conditions, the work rate for first 4 months is much higher that targeted work rate and hence the plant may not be operated under this condition.

Figure 10A:
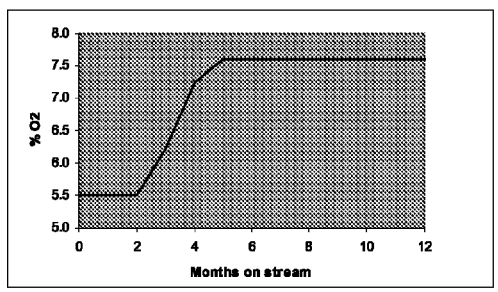
FIG. 10A is a graph depicting the feed gas concentration of oxygen in accordance with an example of a method of maintaining a value of an alkylene oxide production parameter by maintaining feed gas oxygen and alkylene concentrations below target values.
Figure 10B:
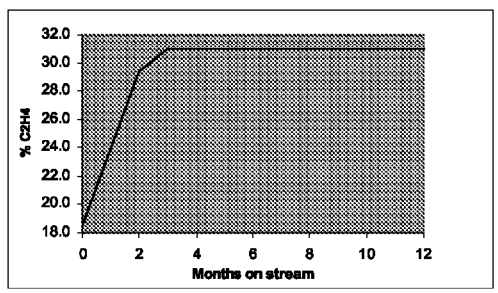
FIG. 10B is a graph depicting the feed gas concentration of ethylene in accordance with the example of FIG. 10A.
Figure 10C:
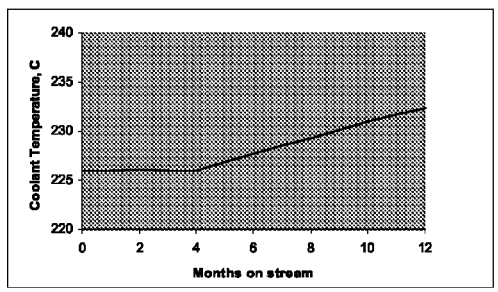
FIG. 10C is a graph depicting reaction temperature as indicated by coolant inlet temperature in accordance with the example of FIG. 10A.
Figure 10D:
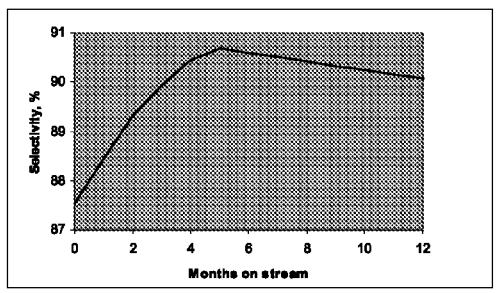
FIG. 10D is a graph depicting efficiency (selectivity) toward the production of ethylene oxide in accordance with the example of FIG. 10A.

Because of the minimum temperature limit $T_{MIN}$ of 226° C., the activity of the high selectivity catalyst needs to be adjusted during the early life of the catalyst. Thus, the feed gas oxygen and ethylene concentrations are initially set below their target values to maintain the target work-rate $AO_T$ of 7.49 lb/(hr-ft3) while operating at the minimum coolant temperature $T_{MIN}$ of 226° C. The results are shown in FIGS. 10A-D. FIGS. 10A and B respectively depict the feed gas oxygen $C_{O2}$ and ethylene $C_A$ concentrations, while FIGS. 10C and D respectively depict the resulting coolant temperature T and efficiency (selectivity). As shown in the figures, the feed gas oxygen concentration $C_{O2}$ is set at 5.5%, which is below its target value $C_{O2T}$ of 7.6%, and the feed gas ethylene concentration $C_A$ is set at 18.5%, which is below its target value $C_{AT}$ of 31%. The starting reaction temperature is the minimum constrained temperature $T_{MIN}$ of 226° C. In this example, the feed gas oxygen concentration $C_{O2}$ is maintained substantially at 5% for a period of two (2) months and is then increased in accordance with three substantially linear functions of differing slopes until reaching the target value $C_{O2T}$ of 7.6% at month five (5). The feed gas ethylene concentration $C_A$ is gradually ramped up from start-up or shortly after (i.e., shortly after ethylene oxide production is first detected) at a substantially constant rate for a period of two (2) months. At the end of the two (2) months, the feed gas ethylene concentration $C_A$ reaches 29%, and its rate of increase adjusted to a lower, yet still substantially constant rate such that at three (3) months after start-up, the target feed gas ethylene concentration $C_{AT}$ of 31% is achieved. As shown in FIG. 10D, the efficiency (selectivity) toward ethylene oxide starts at a value of 87.5% and reaches a maximum of 90.5% by month 5, after which it slowly decreases to a value of 90% over the following seven (7) months.

Example 6

As with the previous example, a simulation is carried out to predict the effects of reducing oxygen and ethylene feed gas concentrations to maintain a desired work rate at a constrained reaction temperature in a process for making ethylene oxide using a high efficiency catalyst. The ethylene oxide work rate is maintained at a constant desired level $AO_T$ of 7.49 lb/(hr-ft3) (i.e., 120 kg ethylene oxide/hr-m³ catalyst). The minimum coolant temperature $T_{MIN}$ is 226° C., and the target values of feed gas alkylene, oxygen, and carbon dioxide concentrations $C_{O2T}$, $C_{AT}$, and $C_{CO2T}$ are the same as in the previous example, as is the gas hourly space velocity. However, in this example, the feed gas oxygen and ethylene concentrations are maintained at their target values $C_{O2T}$, $C_{AT}$ of 7.6% and 31%, respectively, throughout the catalyst life. Thus, to maintain the desired ethylene oxide work rate $AO_T$, the feed gas carbon dioxide concentration $C_{CO2}$ is initially set at 5.8%, higher than its 1.2% target value $C_{CO2T}$.

Figure 11A:
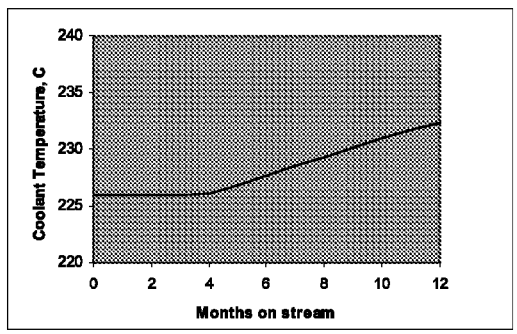
FIG. 11A is a graph depicting reaction temperature as indicated by coolant inlet temperature in accordance with an example of a method of maintaining a value of an alkylene oxide production parameter by maintaining feed gas carbon dioxide concentration above a target value.
Figure 11B:
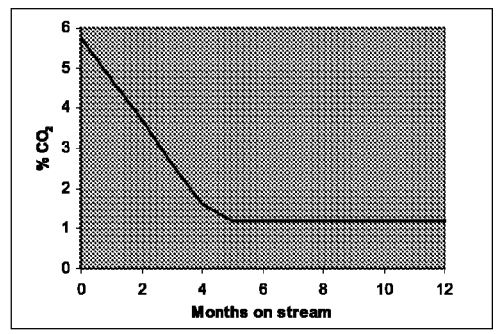
FIG. 11B is a graph depicting the feed gas concentration of carbon dioxide in accordance with the example of FIG. 11A.
Figure 11C:
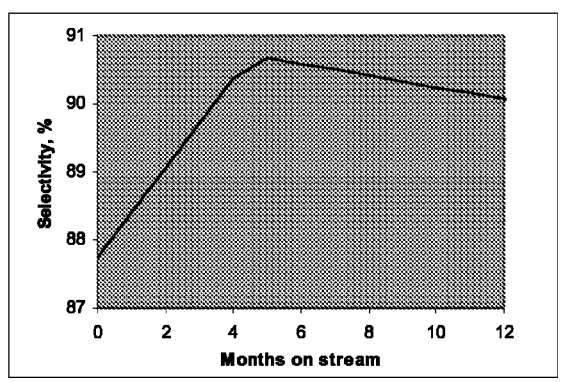
FIG. 11C is a graph depicting efficiency (selectivity) toward the production of ethylene oxide in accordance with the example of FIG. 11C.

FIG. 11A depicts the coolant temperature profile. FIG. 11B depicts the feed gas carbon dioxide concentration profile. As the figure indicates, the feed gas carbon dioxide concentration $C_{CO2}$ is gradually decreased from an initial value of 5.8% to a value of 1.5% within a period of four (4) months. From months four (4) to five (5), the concentration is further decreased until the target feed gas carbon dioxide concentration $C_{CO2T}$ of 1.2% is achieved. As shown in FIG. 11A, the coolant temperature is maintained at the minimum value $T_{MIN}$ of 226° C. for a period of four (4) months and is then increased thereafter. The efficiency toward ethylene oxide is depicted in FIG. 11C. As the figure indicates, the efficiency starts at 87.7% and gradually increases to 90.3% over a period of four (4) months. It then increases to 90.5% over a period of an additional month.

Example 7

Figure 12A:
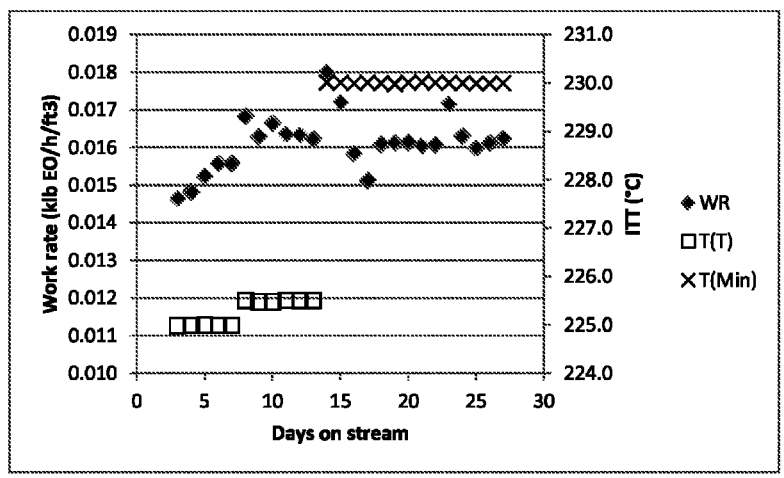
FIG. 12A is a graph depicting the ethylene oxide work rate and reactor temperature for a process of making ethylene oxide using a high efficiency catalyst in a pilot plant reactor used to simulate the situation of a process reactor with a minimum coolant temperature limitation.

An ethylene oxide pilot plant is operated in a manner that simulates a process reactor constrained by a minimum cooling temperature limitation. FIG. 12A depicts work rate and reactor temperature data for the process, and FIG. 12B depicts feed gas concentrations of oxygen, ethylene, and carbon dioxide for the process.

An ethylene oxide reactor with a 0.959 inch (2.44 cm) tube inner diameter is charged with 0.1095 ft3 (3.1 liters) of a high-efficiency, rhenium promoted catalyst. Ethylene oxide work rate is selected as the alkylene oxide production parameter to be monitored, and its target value $AO_T$ is set at 0.016 klb/(hr-ft3 catalyst) (i.e., 256 kg/(hr-m3 catalyst). The target feed gas oxygen concentration $C_{o2T}$ is 8.5%, and the target feed gas ethylene concentration $C_{AT}$ is 40%. Ethane content in the reactant feed is 0.6% and the ethylene chloride concentration in the feed is 2.3 ppm. All concentrations stated herein are on a molar basis unless stated otherwise. The target feed gas carbon dioxide concentration $C_{CO2T}$ is 2.0%, and the reactant flow rate is 645 scfh. The feed gas pressure is 295 psig (2135 kPa absolute). At these target conditions, the reactor temperature $T_1$ required to achieve the target work rate in the pilot plant reactor is 225.5° C. as seen from day 10 to day 13 in FIG. 12A. However, the actual process has a minimum coolant temperature $T_{MIN}$ of 230° C. Considering that 230° C. is the lower limit of coolant temperature, the process reactor cannot be operated below 230° C. Operation at 230° C. at target conditions will result in a work rate which is higher than the target.

Figure 12B:
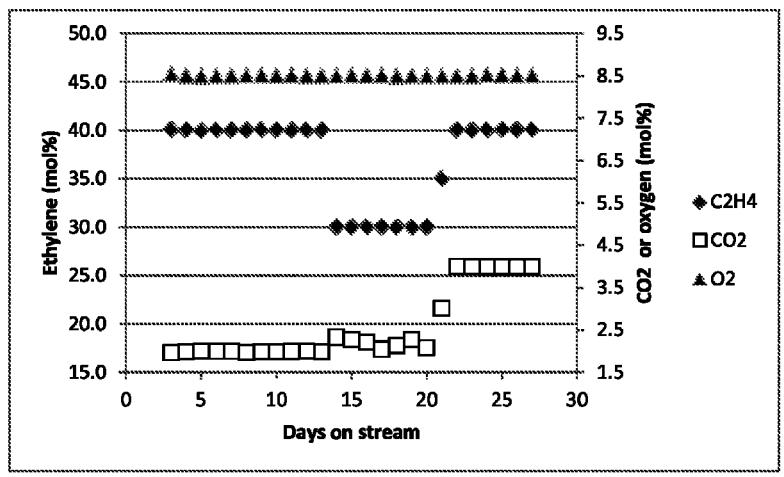
FIG. 12B graph depicting the feed gas molar concentrations of ethylene, oxygen and carbon dioxide in accordance with the example of FIG. 12A. maintained during the experiment of FIG. 12A.

FIGS. 12A-12B (days 14-20) show the effects of lowering the feed gas ethylene concentration below its target value ($C_{AT}$) of 40% while maintaining the feed gas oxygen concentration at its target value ($C_{O2T}$) and the feed gas carbon dioxide concentration at its target value ($C_{CO2T}$) on the reaction temperature and the work rate. With a feed composition of 30% ethylene, 8.5% oxygen, 2% CO2 and 0.6% ethane and 2.9 ppm ECl, the work rate is maintained at its target value from day 14 to day 20 on stream while operating at the constrained reactor temperature $T_{MIN}$.

The data from days 22-27 in FIGS. 12A-12B shows the effects of operating with the feed gas carbon dioxide concentration above its target value ($C_{CO2T}$) of 2.5% while maintaining the feed gas oxygen and ethylene concentrations at their respective target values $C_{O2T}$ and $C_{AT}$. With a feed gas composition of 40% ethylene, 8.5% $O_2$, 4% $CO_2$, 0.6% ethane and 2.9 ppm ECl, the work rated is maintained at its target value from day 22 to day 27 on stream while operating at the constrained reaction temperature 230° C. Thus, Example 7 illustrates the independent use of feed gas ethylene and carbon dioxide concentrations to operate at a constrained reaction temperature while maintaining a desired value of an alkylene oxide production parameter.

What is claimed is:

1. A method of maintaining a desired value of an alkylene oxide production parameter in a process for making the alkylene oxide by reacting a feed gas comprising an alkylene, oxygen, and at least one organic chloride over a high-efficiency silver catalyst, the method comprising the steps of:
    selecting a target value of alkylene concentration in the feed gas and a target value of oxygen concentration in the feed gas, wherein the target value of the alkylene concentration in the feed gas, the target value of the oxygen concentration in the feed gas, and the desired value of the alkylene oxide production parameter correspond to a first reaction temperature; and
    maintaining at least one selected from the group consisting of the alkylene concentration in the feed gas and the oxygen concentration in the feed gas below its corresponding target value to maintain the desired value of the alkylene oxide production parameter at a second reaction temperature greater than the first reaction temperature.

2. The method of claim 1, wherein the second reaction temperature corresponds to a minimum achievable reactor coolant temperature.

3. The method of claim 1, wherein the step of maintaining at least one selected from the group consisting of the alkylene concentration in the feed gas and the oxygen concentration in the feed gas below its corresponding target value further comprises maintaining an overall catalyst chloriding effectiveness at a constant value.

4. The method of claim 1, wherein the step of maintaining at least one selected from the group consisting of the alkylene concentration in the feed gas and the oxygen concentration in the feed gas below its corresponding target value is carried out for a period of no more than one year.

5. The method of claim 1, further comprising reducing the concentration of oxygen in the feed gas to a value above a selected minimum concentration of oxygen in the feed gas if the alkylene oxide production parameter is greater than the desired value of the alkylene oxide production parameter, the second reaction temperature is equal to a minimum achievable reaction temperature, and the concentration of oxygen in the feed gas is greater than the selected minimum oxygen concentration in the feed gas.

6. The method of claim 1 further comprising reducing the concentration of alkylene in the feed gas to a value above a selected minimum concentration of alkylene in the feed gas if the alkylene oxide production parameter is greater than the desired value of the alkylene oxide production parameter, the second reaction temperature is equal to a minimum achievable reaction temperature, and the concentration of alkylene in the feed gas is greater than the selected minimum alkylene concentration in the feed gas.

7. The method of claim 1, further comprising:
  selecting a target value of carbon dioxide concentration in the feed gas;
  maintaining the concentration of carbon dioxide in the feed gas at a value greater than the target value to maintain the desired value of the alkylene oxide production parameter.

8. The method of claim 7, further comprising determining whether the oxygen concentration in the feed gas is greater than a selected minimum concentration of oxygen in the feed gas, determining whether the alkylene concentration in the feed gas is greater than a selected minimum concentration of the alkylene in the feed gas, and wherein the step of maintaining the concentration of carbon dioxide in the feed gas at a value greater than the target value is performed only if the concentration of oxygen in the feed gas is not greater than the selected minimum concentration of oxygen in the feed gas and the concentration of alkylene in the feed gas is not greater than the selected minimum concentration of alkylene in the feed gas.

9. The method of claim 7, wherein the step of maintaining the concentration of carbon dioxide in the feed gas at a value greater than the target value of carbon dioxide concentration in the feed gas comprises maintaining the concentration of carbon dioxide in the feed gas below a maximum value of not more than five (5) mole percent.

10. The method of claim 1, wherein the step of maintaining at least one selected from the group consisting of the alkylene concentration in the feed gas and the oxygen concentration in the feed gas below its corresponding target value comprises maintaining the alkylene concentration in the feed gas at no less than eighteen (18) mole percent.

11. The method of claim 1, wherein the step of maintaining at least one selected from the group consisting of the alkylene concentration in the feed gas and the oxygen concentration in the feed gas below its corresponding target value comprises maintaining the oxygen concentration in the feed gas at no less than its corresponding target value and no less than four (4) mole percent.

12. The method of claim 1, wherein the first reaction temperature is selected to achieve a maximum efficiency toward the production of the alkylene oxide at a selected overall catalyst chloriding effectiveness value, the desired value of the alkylene oxide production parameter, the target concentration of oxygen in the feed gas, the target concentration of alkylene in the feed gas, and a target concentration of carbon dioxide in the feed gas.

13. The method of claim 1, wherein the first reaction temperature corresponds to an optimized combination of reaction temperature and overall catalyst chloriding effectiveness at the target concentration of oxygen in the feed gas, the target concentration of alkylene in the feed gas, and a target concentration of carbon dioxide in the feed gas, and the optimized combination of reaction temperature and overall catalyst chloriding effectiveness is determined by determining the efficiency toward the production of the alkylene oxide at a variety of values of the alkylene oxide production parameter as the overall catalyst chloriding effectiveness is varied over a specified range at a plurality of reaction temperatures.

14. A method of maintaining a desired value of an alkylene oxide production parameter in a process for making the alkylene oxide by reacting a feed gas comprising an alkylene, oxygen, and at least one organic chloride over a high-efficiency silver catalyst, the method comprising the steps of:
  selecting a target value of alkylene concentration in the feed gas, a target value of oxygen concentration in the feed gas, and a target value of carbon dioxide concentration in the feed gas, wherein the target value of the alkylene concentration in the feed gas, the target value of the oxygen concentration in the feed gas, the target value of carbon dioxide concentration in the feed gas, and the desired value of the alkylene oxide production parameter correspond to a first reaction temperature; and
  maintaining the carbon dioxide concentration in the feed gas above its corresponding target value while maintaining the alkylene concentration in the feed gas and the oxygen concentration in the feed gas at or above their corresponding target values to maintain the desired value of the alkylene oxide production parameter at a second reaction temperature greater than the first reaction temperature.

15. The method of claim 14, wherein the second reaction temperature corresponds to a minimum achievable reactor coolant temperature.

* * * * *